United States Patent
Lee et al.

(10) Patent No.: US 7,413,817 B2
(45) Date of Patent: Aug. 19, 2008

(54) 4,4'-BIS(CARBAZOL-9-YL)-BIPHENYL BASED SILICONE COMPOUND AND ORGANIC ELECTROLUMINESCENT DEVICE USING THE SAME

(75) Inventors: Seok Jong Lee, Suwon-si (KR); Young-Kook Kim, Suwon-si (KR); Seok-Hwan Hwang, Suwon-si (KR)

(73) Assignee: Samsung SDI Co., Ltd., Suwon-si (KR)

( * ) Notice: Subject to any disclaimer, the term of this patent is extended or adjusted under 35 U.S.C. 154(b) by 388 days.

(21) Appl. No.: 10/876,843

(22) Filed: Jun. 28, 2004

(65) Prior Publication Data

US 2005/0064238 A1 Mar. 24, 2005

(30) Foreign Application Priority Data

Sep. 22, 2003 (KR) ...................... 10-2003-0065538

(51) Int. Cl.
  *H01L 51/54* (2006.01)
  *C07D 209/82* (2006.01)
  *C07F 7/08* (2006.01)
(52) U.S. Cl. .................. 428/690; 428/917; 313/504; 313/506; 257/40; 257/E51.046; 257/E51.05; 548/440; 556/413; 556/465; 562/899
(58) Field of Classification Search .................. 562/899
  See application file for complete search history.

(56) References Cited

U.S. PATENT DOCUMENTS

| 6,310,231 B1 * | 10/2001 | Igarashi et al. ............. 556/489 |
| 7,011,871 B2 * | 3/2006 | Herron et al. ................ 428/1.4 |
| 2002/0028329 A1 * | 3/2002 | Ise et al. ..................... 428/336 |
| 2002/0125818 A1 | 9/2002 | Sato et al. ................... 313/504 |
| 2005/0214572 A1 * | 9/2005 | Ogasawara et al. ......... 428/690 |

FOREIGN PATENT DOCUMENTS

| JP | 2000-351966 | 12/2000 |
| JP | 2002-100476 | 4/2002 |
| JP | 2002-329579 | 11/2002 |
| JP | 2003-243178 | 8/2003 |
| JP | 2004-200103 | 7/2004 |
| JP | 2004-200104 | 7/2004 |

OTHER PUBLICATIONS

ShiWei Yin, Z. Shuai, and Yilin Wang; A Quantitative Structure-Property Relationship Study of the Glass Transition Temperature of OLED Materials; 10.1021/ci034011y; 2003 American Chemical Society Published on Web Apr. 3, 2003; pp. 970-977, J. Chem. Inf. Comput. Sci. (43).

Chihaya Adachi et al.; Endothermic energy transfer: A mechanism for generating very efficient high-energy phosphorescent emission in organic materials; 2001 American Institute of Physics, Applied Physics Letters; vol. 79, No. 13; Sep. 24, 2001; pp. 2082-2084.

First Office Action issued Dec. 7, 2007 by the Patent Office of the People's Republic of China re: Chinese Application No. 200410057867.7.

\* cited by examiner

*Primary Examiner*—Marie R. Yamnitzky
(74) *Attorney, Agent, or Firm*—Stein, McEwen & Bui, LLP

(57) ABSTRACT

A 4,4'-Bis(carbazol-9-yl)-biphenyl (CBP) based silicone compound and an organic electroluminescent device using the CBP based silicon compound have excellent blue light emission characteristics and hole transfer capability. The CBP based silicon compound may be used as a blue light emission material or as a host material for various phosphorescent or fluorescent dopants emitting red, green, blue, or white light. Therefore, the organic electroluminescent device using the CBP based silicon compound has excellent characteristics such as a high efficiency, a high luminance, a long life span, and a low power consumption.

17 Claims, 7 Drawing Sheets

4,4'-BIS(CARBAZOL-9-YL)-BIPHENYL BASED SILICONE COMPOUND AND ORGANIC ELECTROLUMINESCENT DEVICE USING THE SAME

CROSS-REFERENCE TO RELATED APPLICATIONS

This application claims the priority of Korean Patent Application No. 2003-65538, filed on Sep. 22, 2003, in the Korean Intellectual Property Office, the disclosure of which is incorporated herein by reference in its entirety.

BACKGROUND OF THE INVENTION

1. Field of the Invention

The present invention relates to a 4,4'-Bis(carbazol-9-yl)-biphenyl (CBP) based silicone compound and an organic electroluminescent device using the same. More particularly, the present invention relates to a CBP based compound that may be used as a host material for various phosphorescent or fluorescent dopants emitting red, green, blue, or white light, and an organic electroluminescent device using the CBP based compound which has enhancements such as, for example, high efficiency, high luminance, long life span, and low power consumption.

2. Description of the Related Art

Electroluminescent devices (EL devices) are self emission type display devices that have advantages such as a wide viewing angle, superior contrast, and fast response speed.

The EL devices are classified into inorganic EL devices and organic EL devices according to the material utilized in a light-emitting layer. The organic EL devices have advantages over the inorganic EL devices, such as high luminance, low driving voltage, fast response speed, and multi-coloration.

Generally, the organic EL devices have a sequentially stacked structure of an anode, a hole transport layer, a light-emitting layer, an electron transport layer, and a cathode on a substrate. The hole transport layer, the light-emitting layer, and the electron transport layer are organic films comprising an organic compound.

The organic EL devices having the above-described structure are driven in accordance with the following principle.

When a voltage is applied to the anode and the cathode, holes from the anode migrate toward the light-emitting layer via the hole transport layer. On the other hand, electrons from the cathode are injected into the light-emitting layer via the electron transport layer. Thereafter, the electrons and the holes recombine with each other at the light-emitting layer to generate excitons. When the excitons are converted from an excited state to a ground state, a fluorescent molecule of the light-emitting layer emits light, which displays an image. Here, light emission through conversion from a singlet excited state to a ground state is called "fluorescence", and light emission through conversion from a triplet excited state to a ground state is called "phosphorescence." With respect to fluorescence, the proportion of singlet excited state is 25% (the proportion of triplet excited state is 75%), and thus, there is a limitation on light emission efficiency. On the other hand, with respect to phosphorescence, the triplet excited state and the singlet excited state may be used. Therefore, a theoretical internal quantum efficiency may reach 100%.

By way of an example of an organic electroluminescent device using phosphorescence, a highly efficient, green and red-emitting organic electroluminescent device may use a CBP based host, and a phosphorescent dopant such as Ir(ppy)$_3$ (ppy is phenylpyridine) and PtOEP (platinum(II) octaethylporphyrin) having heavy elements with significant spin-orbit coupling such as Ir and Pt in the center thereof may be utilized. However, the organic electroluminescent device has a short life span of 150 hours or less since CBP has a low glass transition temperature of less than 110° C. and is easily crystallized, which makes it difficult to provide a commercially suitable product.

As another example of an organic electroluminescent device using phosphorescence, an organic electroluminescent device uses a blue phosphorescent dopant (4,6-F$_2$ppy)$_2$Irpic with a fluorinated ppy ligand structure. The energy band gap between the triplet state and the ground state of CBP is high enough to provide an energy transition for green and red phosphorescent dopants, but is smaller than the energy band gap of a blue phosphorescent dopant. Therefore, it is reported that a very inefficient endothermic energy transition, not an exothermic energy transition, occurs even when a material such as (4,6-F$_2$ppy)$_2$Irpic with photoluminescent (PL) peaks at 475 nm and 495 nm is used. For this reason, the CBP based host cannot provide a sufficient energy transition for a blue phosphorescent dopant, thus causing problems such as low-efficiency blue light emission and a short life span.

In addition, U.S. patent application Laid-Open Publication No. 2002/0125818 A1 discloses an organic electroluminescent device using a CBP based compound.

Recently, a mCP (1,3-Bis(carbazol-9-yl)-benzene) compound having a triplet energy band gap higher than CBP has been used. However, the mCP compound has problems such as a molecular weight that is too small and a low stability. In this regard, to obtain high-efficiency blue light emission characteristics exhibiting a long lifetime, it is very beneficial to develop a host material with a triplet energy band gap that is larger than the triplet energy band gap of CBP for efficient energy transition for a blue-emitting dopant and which has a high glass transition temperature (Tg).

SUMMARY OF THE INVENTION

The present invention provides a host material suitable for fluorescent and phosphorescent dopants, emitting a full color including red, green, blue, and white color, which has a high electrical stability, a high charge transport capability, and a high glass transition temperature, and prevents crystallization.

The present invention also provides an organic electroluminescent device having a high efficiency, low voltage, high luminance, and long life span by using the host material.

According to an aspect of the present invention, a compound is represented by Formula 1 below:

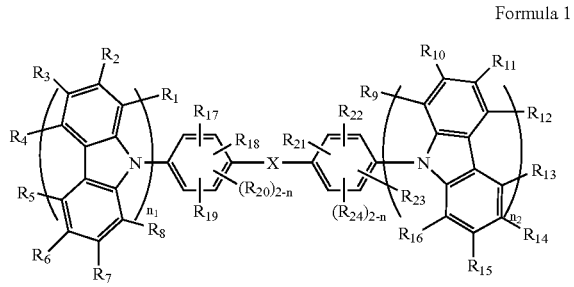

Formula 1 wherein:

$n_1$ and $n_2$ are independently 1 or 2,

X is —Si(A$_1$)(A$_2$)- or Se, and

A$_1$, A$_2$, and R$_1$ to R$_{24}$ are independently a hydrogen atom, a substituted or unsubstituted alkyl group of C$_1$-C$_{30}$, a substituted or unsubstituted acyl group of C$_1$-C$_{30}$, a substituted or unsubstituted alkoxycarbonyl group of C$_1$-C$_{30}$, a substituted or unsubstituted alkoxy group of C$_1$-C$_{30}$, a substituted or unsubstituted alkenyl group of $C_2$-$C_{30}$, a substituted or unsubstituted alkynyl group of $C_2$-$C_{30}$, a substituted or unsubstituted alkylcarboxyl group of $C_2$-$C_{30}$, a substituted or unsubstituted aryl group of $C_6$-$C_{30}$, a substituted or unsubstituted aralkyl group of $C_6$-$C_{30}$, a substituted or unsubstituted aralkyloxy group of $C_6$-$C_{30}$, a substituted or unsubstituted heteroaryl group of $C_2$-$C_{30}$, a substituted or unsubstituted heteroaryloxy group of $C_2$-$C_{30}$, a substituted or unsubstituted aryloxy group of $C_6$-$C_{30}$, a substituted or unsubstituted cycloalkyl group of $C_4$-$C_{30}$, —N(R)(R') provided that R and R' are independently a hydrogen, an alkyl group of $C_1$-$C_{30}$, an aryl group of $C_6$-$C_{30}$, or a heteroaryl group of $C_2$-$C_{30}$), cyano, hydroxy, or carboxyl, or at least an adjacent two of $R_1$ to $R_{24}$ are connectable to form a ring.

According to another aspect of the present invention, an organic electroluminescent device comprises an organic film between a pair of electrodes, wherein the organic film comprises the above-described compound.

Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE PREFERRED EMBODIMENTS

Figure 1:
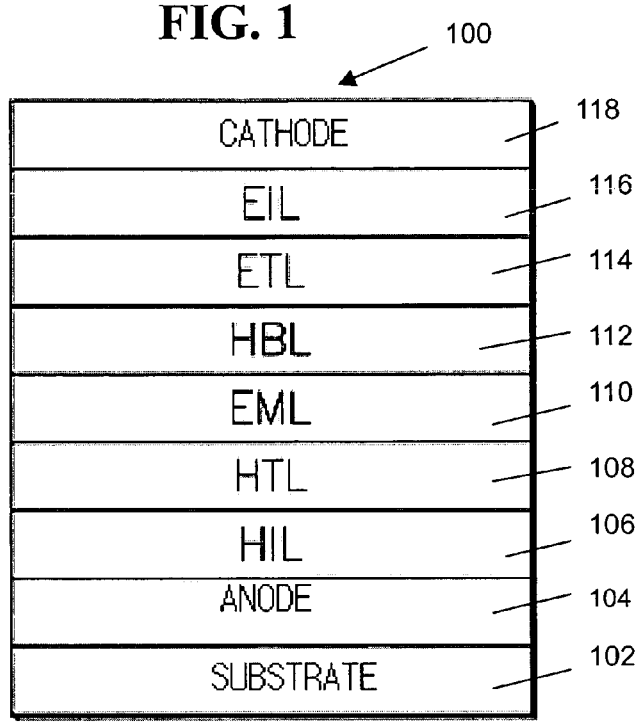
FIG. 1 is a sectional view of a conventional organic electroluminescent device in accordance with an embodiment of the present invention.

Reference will now be made in detail to the embodiments of the present invention, examples of which are illustrated in the accompanying drawings, wherein like reference numerals refer to the like elements throughout. The embodiments are described below to explain the present invention by referring to the figures.

The compound represented by Formula 1 according to an embodiment of the present invention is a blue light emission material and exhibits blue light emission characteristics that are darker than the blue light emission characteristics of conventional molecules. Therefore, the compound represented by Formula 1 may be used as a blue host material for a full color organic electroluminescent device. In particular, the compound is useful as a blue phosphorescent host with a triplet energy band gap and a thermal stability suitable for a blue phosphorescent dopant containing a metal such as Ir, Pt, Os, and/or Re. In addition, the compound may be used as a host material for various phosphoresecent or fluorescent dopants emitting red, green, blue, or white light. Therefore, an organic electroluminescent device having a high efficiency, a high luminance, a long life span, and a low power consumption may be obtained.

In Formula 1, as described above, at least an adjacent two of $R_1$ to $R_{24}$ may be interconnected to form a ring. For example, any pair of adjacent substituents such as $R_1$ and $R_2$, $R_2$ and $R_3$, $R_3$ and $R_4$, $R_5$ and $R_6$, $R_6$ and $R_7$, and $R_7$ and $R_8$ may independently form a benzene ring or a cyclohexane ring.

A representative of the compound of Formula 1 may be a compound of Formula 2 or 3 below:

Formula 2

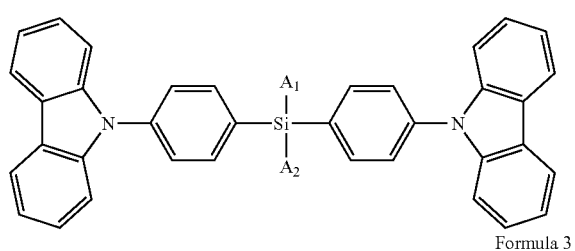

Formula 3

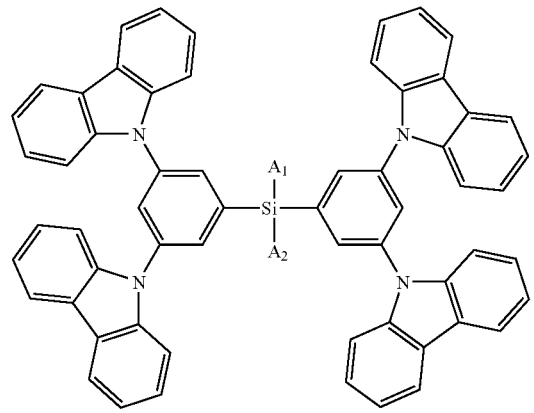

wherein, $A_1$ and $A_2$ are as defined above.

Examples of the compound of Formula 2 or 3 include the compounds represented by Formulas 4 to 18 below:

Formula 4

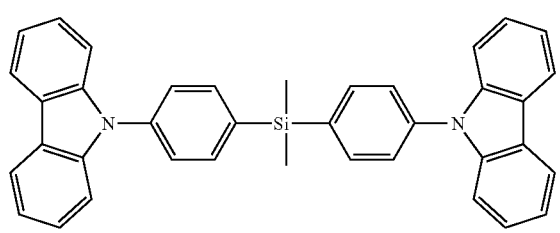

Formula 5
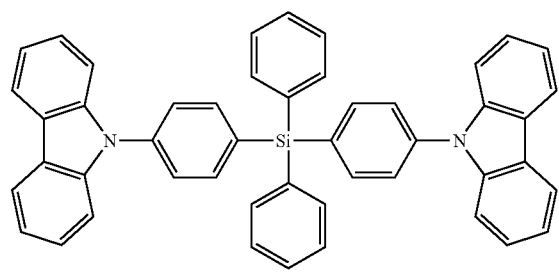
Formula 6
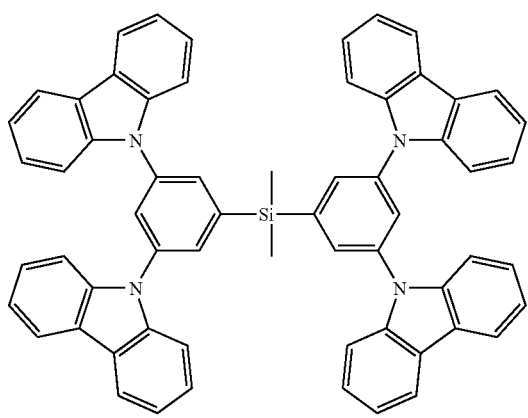
Formula 7
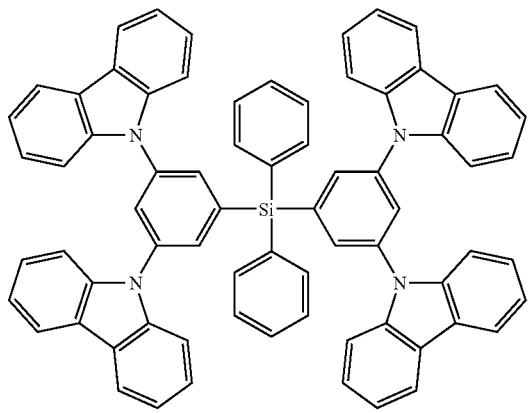
Formula 8
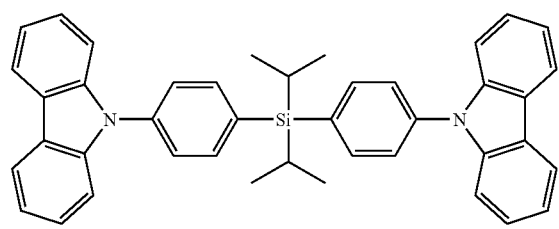
Formula 9
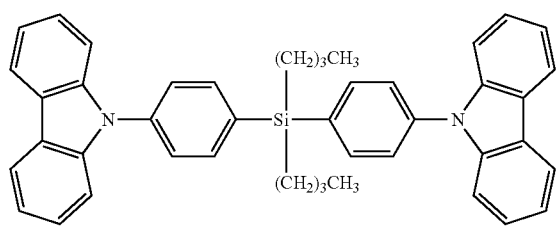
Formula 10
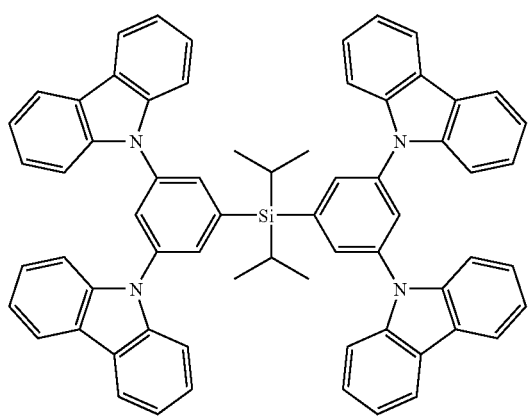
Formula 11
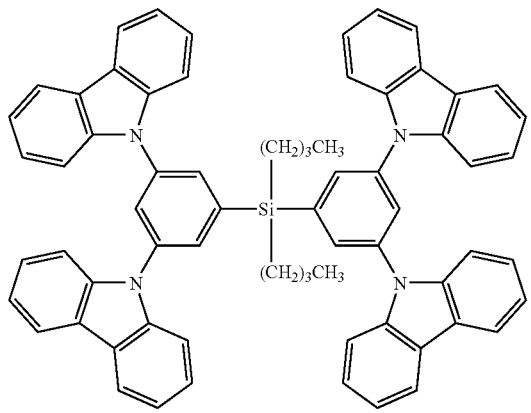
Formula 12
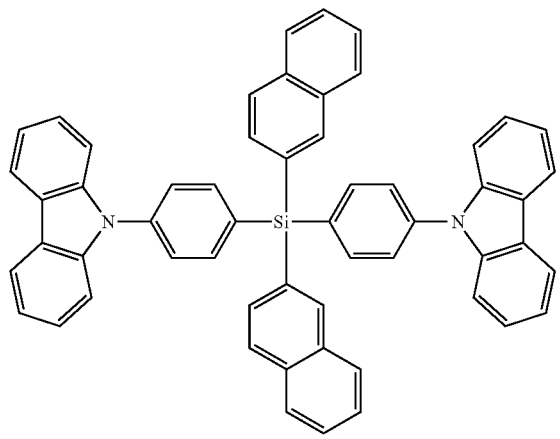

Formula 13
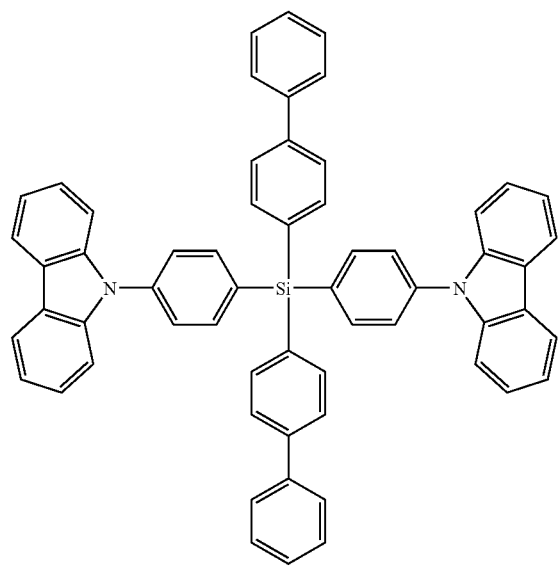
Formula 14
Formula 15
Formula 16
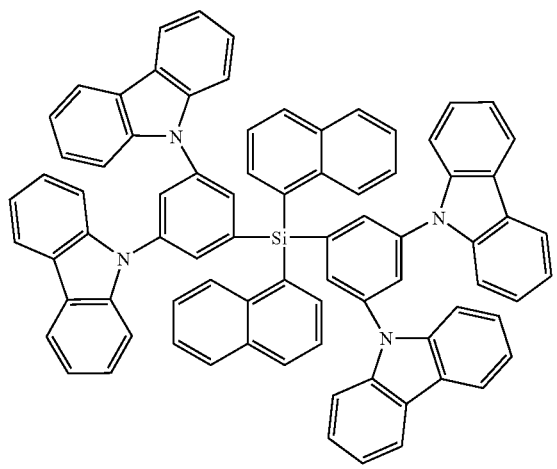
Formula 17
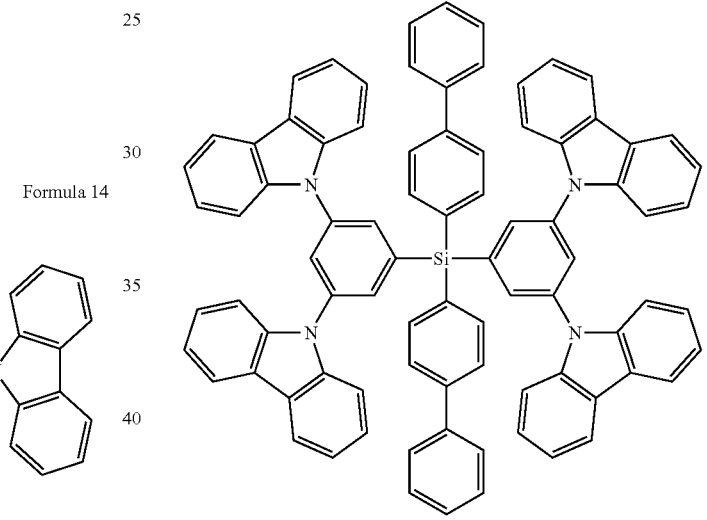
Formula 18
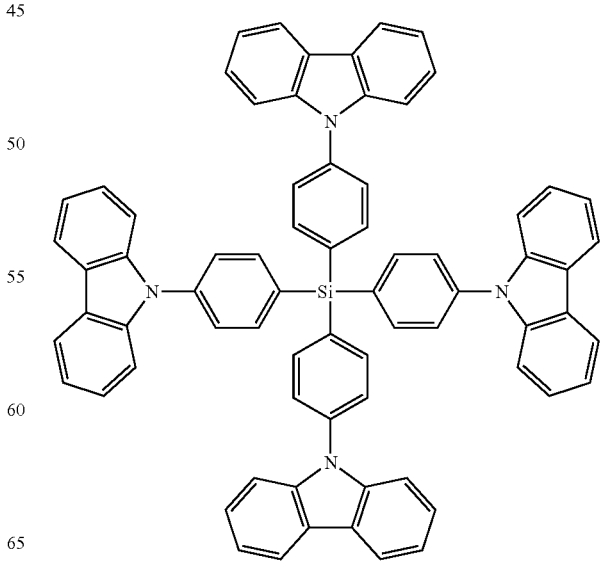

Examples of an unsubstituted alkyl group of $C_1$-$C_{30}$, as used in Formulas 1 to 3, include methyl, ethyl, propyl, isobutyl, sec-butyl, pentyl, iso-amyl, and hexyl. One or more hydrogen atoms of the alkyl group may be substituted with a halogen atom, a hydroxy group, a nitro group, a cyano group, an amino group, an amidino group, a hydrazine group, a hydrazone group, a carboxyl group or its salt, a sulfonyl group or its salt, a phosphoryl group or its salt, an alkyl group of $C_1$-$C_{30}$, an alkenyl group of $C_1$-$C_{30}$, an alkynyl group of $C_1$-$C_{30}$, an aryl group of $C_6$-$C_{30}$, an arylalkyl group of $C_7$-$C_{20}$, a heteroaryl group of $C_2$-$C_{20}$, or a heteroarylalkyl group of $C_3$-$C_{30}$.

Examples of an unsubstituted acyl group of $C_1$-$C_{30}$, as used in Formulas 1 to 3, include acetyl, ethylcarbonyl, isopropylcarbonyl, phenylcarbonyl, naphthylenecarbonyl, diphenylcarbonyl, and cyclohexylcarbonyl. One or more hydrogen atoms of the acyl group may be substituted with the same substituent as in the above-described alkyl group.

Examples of an unsubstituted alkoxycarbonyl group of $C_2$-$C_{30}$, as used in Formulas 1 to 3, include methoxycarbonyl, ethoxycarbonyl, phenyloxycarbonyl, cyclohexyloxycarbonyl, naphthyloxycarbonyl, and isopropyloxycarbonyl. One or more hydrogen atoms of the alkoxycarbonyl group may be substituted with the same substituent as in the above-described alkyl group.

Examples of an unsubstituted alkoxy group of $C_1$-$C_{30}$, as used in Formulas 1 to 3, include methoxy, ethoxy, phenyloxy, cyclohexyloxy, naphthyloxy, isopropyloxy, and diphenyloxy. One or more hydrogen atoms of the alkoxy group may be substituted with the same substituent as in the above-described alkyl group.

The term "unsubstituted alkenyl group of $C_2$-$C_{30}$," as used in Formulas 1 to 3, indicates a radical that contains one or more carbon-carbon double bonds at a center or end of the alkyl group as defined above. Examples of the unsubstituted alkenyl group of $C_2$-$C_{30}$ include ethylene, propylene, butylene, and hexylene. One or more hydrogen atoms of the alkenyl group may be substituted with the same substituent as in the above-described alkyl group.

The term "unsubstituted alkynyl group of $C_2$-$C_{30}$," as used in Formulas 1 to 3, indicates a radical that contains one or more carbon-carbon triple bonds at a center or an end of the alkyl group as defined above. Examples of the unsubstituted alkynyl group of $C_2$-$C_{30}$ include acetylene, propylene, phenylacetylene, naphthylacetylene, isopropylacetylene, t-butylacetylene, and diphenylacetylene. One or more hydrogen atoms of the alkynyl group may be substituted with the same substituent as in the above-described alkyl group.

Examples of the unsubstituted alkylcarboxyl group of $C_2$-$C_{30}$, as used in Formulas 1 to 3, include a methylcarboxyl group, an ethylcarboxyl group, a phenylcarboxyl group, a cyclohexylcarboxyl group, a naphthylcarboxyl group, and an isopropylcarboxyl group. One or more hydrogen atoms of the alkylcarboxyl group may be substituted with the same substituent as in the above-described alkyl group.

The term "unsubstituted aryl group," as used in Formulas 1 to 3, indicates a $C_6$ to $C_{30}$ carbocyclic aromatic system containing one or more rings, wherein such rings may be attached together in a pendant manner or may be fused. The term, "aryl" includes an aromatic radical such as phenyl, naphthyl, and tetrahydronaphthyl. One or more hydrogen atoms of the aryl group may be substituted with the same substituent as in the above-described alkyl group.

Examples of the unsubstituted aryloxy group, as used in Formulas 1 to 3, includes phenyloxy, naphthyloxy, and diphenyloxy. One or more hydrogen atoms of the aryloxy group may be substituted with the same substituent as in the above-described alkyl group.

The term "unsubstituted aralkyl group," as used in Formulas 1 to 3, indicates the above-defined aryl group having a lower alkyl substituents for some hydrogen atoms. Examples of the unsubstituted aralkyl group include benzyl and phenylethyl. One or more hydrogen atoms of the aralkyl group may be substituted with the same substituent as in the above-described alkyl group.

The term "unsubstituted heteroaryl group," as used herein, indicates a 5-30 membered aromatic cyclic system containing one, two, or three of hetero atoms selected from N, O, P, and S. One or more hydrogen atoms of the heteroaryl group may be substituted with the same substituent as in the above-described alkyl group.

The term "unsubstituted heteroaryloxy group," as used herein, indicates the above defined heteroaryl group containing oxygen. Examples of the unsubstituted heteroaryloxy group include benzyloxy and phenylethyloxy. One or more hydrogen atoms of the heteroaryloxy group may be substituted with the same substituent as in the above-described alkyl group.

An example of an unsubstituted aralkyloxy group, as used herein, is benzyloxy group. One or more hydrogen atoms of the aralkyloxy group may be substituted with the same substituent as in the above-described alkyl group.

The term "unsubstituted heteroaralkyl group," as used herein, indicates the heteroaryl group having an alkyl substituent. One or more hydrogen atoms of the heteroaralkyl group may be substituted with the same substituent as in the above-described alkyl group.

Examples of the unsubstituted cycloalkyl group, as used herein, include the cyclohexyl group and the cyclopentyl group. One or more hydrogen atoms of the cycloalkyl group may be substituted with the same substituent as in the above-described alkyl group.

Examples of —N(R)(R'), as used herein, include an amino group and a dimethylamino group.

The compound represented by Formula 1 may be synthesized by various reaction pathways known in the pertinent art. An example of such reaction pathways is as follows.

First, carbazole (A) reacts with phenyl halide (B) to produce a compound (C), as shown in Scheme 1 below.

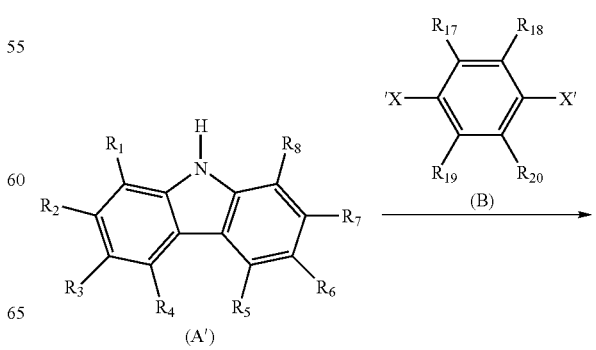

-continued

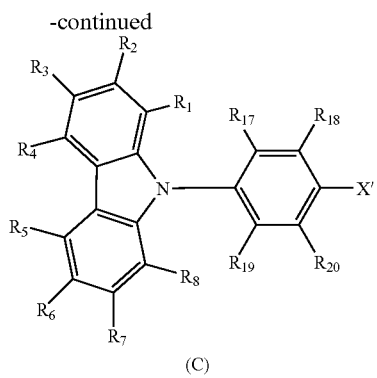

(C)

wherein, X' is —Cl, —Br, or —I, and $R_1$ to $R_8$, and $R_{17}$ to $R_{20}$ are as defined above.

Next, the compound (C) reacts with an organic lithium compound such as n-butyllithium, and then silicone halogenide such as $(A_1)(A_2)SiX'_2$ to produce the compound represented by Formula 1, as shown in Scheme 2 below.

Scheme 2

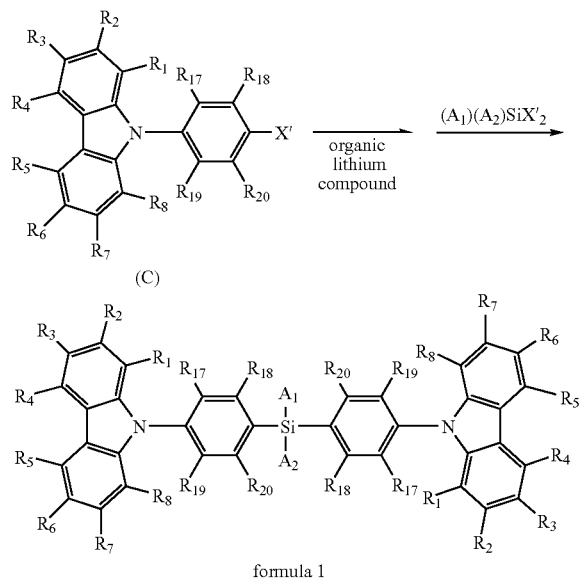

formula 1 wherein, X' is —Cl, —Br, or —I, $A_1$ and $A_2$, $R_1$ to $R_8$, and $R_{17}$ to $R_{20}$ are as defined above.

Hereinafter, an organic electroluminescent device using the compound represented by Formula 1 as a material for an organic film, and a method of manufacturing the same will be described in detail.

FIG. 1 is a sectional view of an organic electroluminescent (EL) device 100 in accordance with an embodiment of the present invention. First, an anode material is coated on an upper surface of a substrate 102 to form an anode 104. Here, the substrate 102 may be a substrate used in a conventional organic EL device. It is preferable to use a glass substrate or a transparent plastic substrate with excellent transparency, surface smoothness, a facilitated handling property, and a waterproof property. The anode material may be indium tin oxide (ITO), indium zinc oxide (IZO), tin oxide ($SnO_2$), or zinc oxide (ZnO), all of which are transparent and conductive.

A hole injection material is applied to an upper surface of the anode by vacuum thermal deposition or spin coating to form a hole injection layer (HIL) 106. Although there are no particular limitations on the hole injection material, it is preferable to use copper phthalocyanine (CuPc), or Starburst amines such as TCTA, m-MTDATA, and m-MTDAPB. Here, TCTA, m-MTDATA, and m-MTDAPB have chemical Formulas shown in J. Chem. Inf. Comput. Sci. 2003, vol. 43, pp. 970-977.

Next, a hole transport material is applied to an upper surface of the hole injection layer by vacuum thermal deposition or spin coating to form a hole transport layer (HTL) 108. Although there are no particular limitations on the hole transport material, it is preferable to use N,N'-bis(3-methylphenyl)-N,N'-diphenyl-4,4'-diamine (TPD), or N,N'-di(naphthalene-1-yl)-N,N'-diphenyl benzidine.

A light-emitting layer (EML) 110 is formed on an upper surface of the hole transport layer 108 thus formed. There are no particular limitations on a material for the light-emitting layer 110. The compound of Formula 1 may be used in alone or may be used as a host material, together with a visible light phosphorescent or fluorescent dopant.

The fluorescent dopant may be IDE102 or IDE105, which are commercially available from IDEMITSU CO., and the phosphorescent dopant may be Ir(ppy)$_3$ (ppy is phenylphyridine) (green light), (4,6-F2ppy)$_2$Irpic et al. (Chihaya Adachi etc., Appl. Phys. Lett., 79, 2082-2084, 2001), TEB002 (COVION CO.), or PtOEP (platinum(II) octaethylporphyrin).

The method of forming the light-emitting layer may vary according to the light-emitting material. For example, vacuum thermal deposition may be used.

The dopant is used in an amount of 0.1 to 20 parts by weight, preferably 0.5 to 12 parts by weight, based on 100 parts by weight of the light-emitting material, i.e., the total weight of the host compound of Formula 1 and the dopant. If the content of the dopant is less than 0.1 parts by weight, an addition effect is insufficient. On the other hand, if the content of the dopant exceeds 20 parts by weight, phosphorescence and fluorescence are too weak due to concentration quenching.

An electron transport material is applied to the light-emitting layer by vacuum deposition or spin coating to form an electron transport layer (ETL) 114. Although there are no particular limitations on the electron transport material, it is preferable to use Alq$_3$ (tris(8-quinolinolato)-aluminium) represented by following formula, BCP (2,9-dimethyl-4,7-diphenylphenanthroline), TAZ (3-phenyl-4-(1'-naphthyl)-5-phenyl-1,2,4-triazole), or OXD7 (1,3-bis(N,N-t-butyl-phenyl)-1,3,4-oxadiazole). When a phosphorescent dopant is used in the formation of the light-emitting layer to prevent the diffusion of triplet excitons or holes into the electron transport layer, a hole blocking material may be further applied to the light-emitting layer by vacuum thermal deposition to form a hole blocking layer (HBL) 112, as shown in FIG. 1. Although there are no particular limitations on the hole blocking material, it is preferable to use the hole blocking material having an electron transport capability and an ionic potential higher than the light-emitting material. A representative of the hole blocking material is Balq, as represented by following formula or phenanthrolines (for example: BCP, UDC Co.).

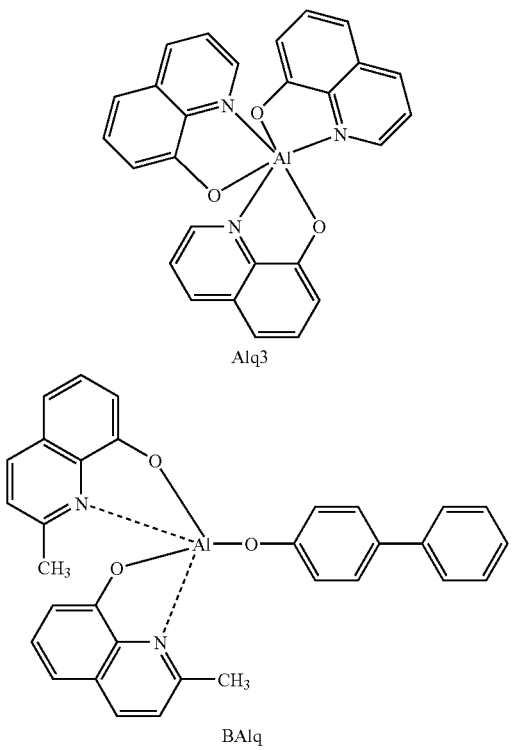

Alq3

BAlq

Then, an electron injection layer (EIL) 116 may be deposited on the electron transport layer, as shown in FIG. 1. Examples of an electron injection material include LiF, NaCl, CsF, Li$_2$O, and BaO.

Finally, a metal for forming cathode is formed on the electron injection layer by vacuum thermal deposition to form a cathode 118. Accordingly, an organic EL device is completed. The metal may be lithium (Li), magnesium (Mg), aluminum (Al), aluminum-lithium (Al—Li), calcium (Ca), magnesium-indium (Mg—In), or magnesium-silver (Mg—Ag). The cathode for a front emission type organic electroluminescent device may, for example, be a light-transmissible cathode made of a transparent material, such as ITO and IZO.

The CBP based silicon compound of Formula 1 may be used as the material for the hole transport layer 108 or the hole injection layer 106, due to a superior hole transport capability, in addition to being utilized as the material for the light-emitting layer 110, as described above.

The organic EL device of the present invention may include one or more intermediate layers between the anode 104, the hole injection layer 106, the hole transport layer 108, the light-emitting layer 110, the hole blocking layer 112, the electron transport layer 114, the electron injection layer 116, and the cathode 118, when needed.

Hereinafter, the present invention will be described more specifically by the following Syntheses and Examples. However, the following Syntheses and Examples are provided only for illustrations and thus the present invention is not limited to or by them.

Synthesis 1. Preparation of Compounds of Formulas 4 and 5

A compound of Formula 4 and a compound of Formula 5 were synthesized according to the reaction pathways shown in Scheme 3 below.

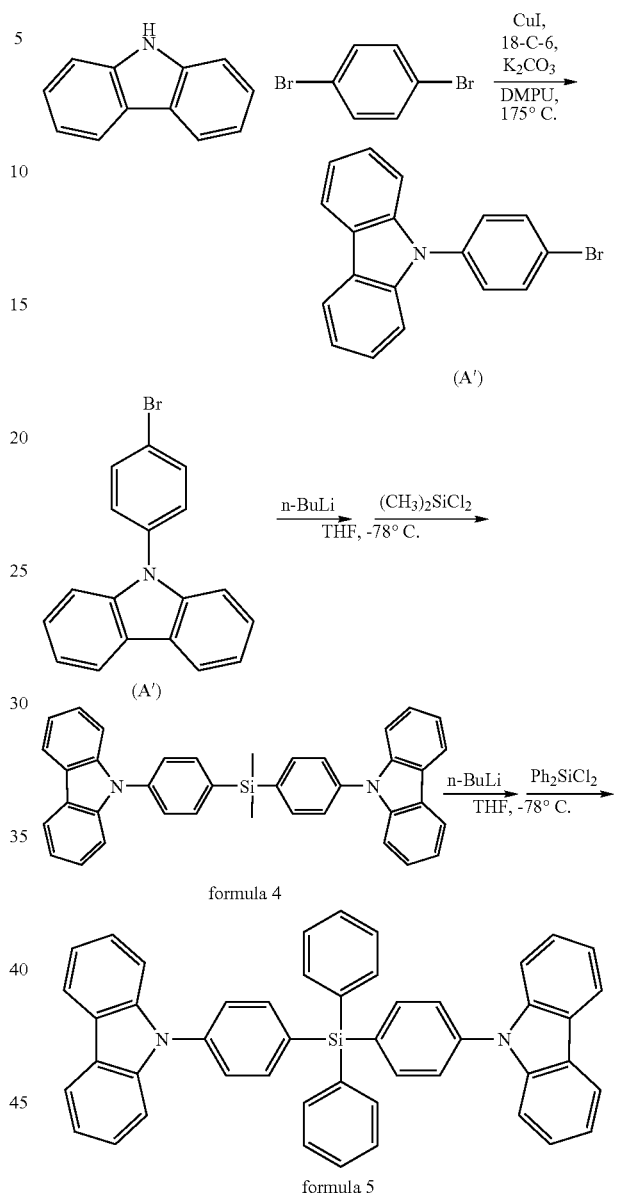

Scheme 3 formula 4 formula 5

Synthesis of Intermediate (A')

Carbazole (335 mg, 2 mmol), 1,4-dibromobenzene (1.2 g, 5 mmol), CuI (76 mg, 0.4 mmol), K$_2$CO$_3$ (1.1 g, 8 mmol), and 18-Crown-6 (10 mg, 0.04 mmol) were dissolved in DMPU (1,3-Dimethyl-3,4,5,6-tetrahydro-(1H)-pyrimidinone) (5 mL), and then were heated at 170° C. for 8 hours. The resultant mixture was cooled to room temperature, and the solids were filtered. After the filtration, a little ammonia water was added to a filtrate, and the filtrate was extracted three times with diethylether (10 mL), and the thus-obtained diethylether layer was combined. The combined diethylether layer was dried over MgSO$_4$, and then was dried under reduced pressure to obtain a crude product. The crude product was purified by silica-gel column chromatography to give the intermediate (A') as a white solid (480 mg, yield 75%) and had the following spectrum: $^1$H-NMR (CDCl$_3$, 400MHz) δ (ppm) 8.12 (d, 2H), 7.70 (d, 2H), 7.43-7.34 (m, 6H), 7.30-7.26 (m, 2H).

Synthesis of Compound of Formula 4

The intermediate (A') (2 g, 6.29 mmol) was dissolved in THF (20 mL) and n-buthyllithium (2.75 mL, 7.2 mmol, 2.5 equiv.) in n-hexane at −78° C. was then dropwise added thereto, followed by stirring for one hour. Dichloromethylsilane (0.365 mL, 3.0 mmol) was added to the resultant mixture, and the resulting mixture was stirred at room temperature for 5 hours.

When the reaction was completed, an ammonium hydroxide solution (1 ml) was added to the reaction mixture, stirred for one hour, and extracted three times with ethylacetate (20 mL). A combined ethylacetate layer was dried over $MgSO_4$, and a solvent was removed. An obtained residue was dissolved in a mixed solvent (1:4 by volume) of ethylacetate and n-hexane and filtered to give the compound of Formula 4 as a white solid (1.2 g, yield 74%), which had the following spectra: $^1$H-NMR ($CDCl_3$, 300MHz) δ (ppm) 8.14 (d, 4H), 7.83 (d, 4H), 7.62 (d, 4H), 7.49 (d, 4H), 7.41 (dt, 4H), 7.29 (dt, 4H), 0.773 (s, 6H) and $^{13}$C NMR (CDCl3, 100 MHz) δ (ppm) 140.7, 138.7, 137.1, 135.7, 126.3, 125.9, 123.5, 120.3, 120.3, 120.0, 109.9, −2.2.

Figure 2:
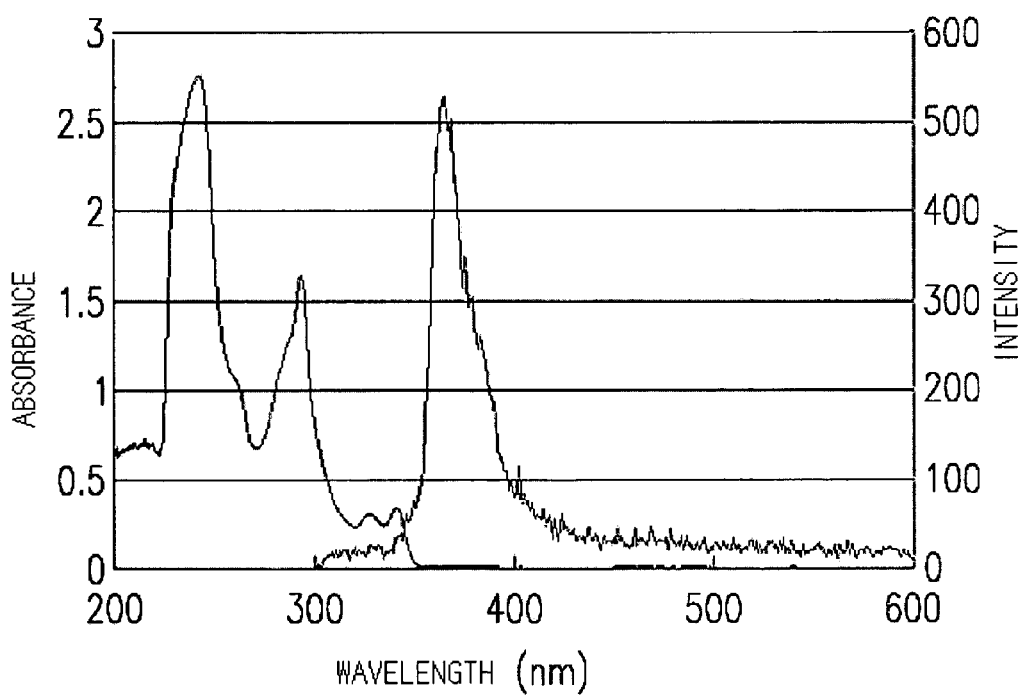
FIG. 2 is a photoluminescent (PL) spectrum of a solution containing a compound of Formula 4.

The compound of Formula 4 was diluted to 0.2 mM in $CHCl_3$, and a UV spectrum was measured. The UV spectrum of the diluted solution showed the maximal absorbance at 293 nm. Also, the compound of Formula 4 was diluted to 10 mM in $CHCl_3$ and a photoluminescent (PL) spectrum was measured at 293 nm. The PL spectrum of the diluted solution showed the maximal light intensity at 364 nm (FIG. 2). Color purity corresponded to the CIE coordinate of x=0.2534, y=0.3029 in NTSC (National Television System Committee) chromaticity diagram.

Figure 3:
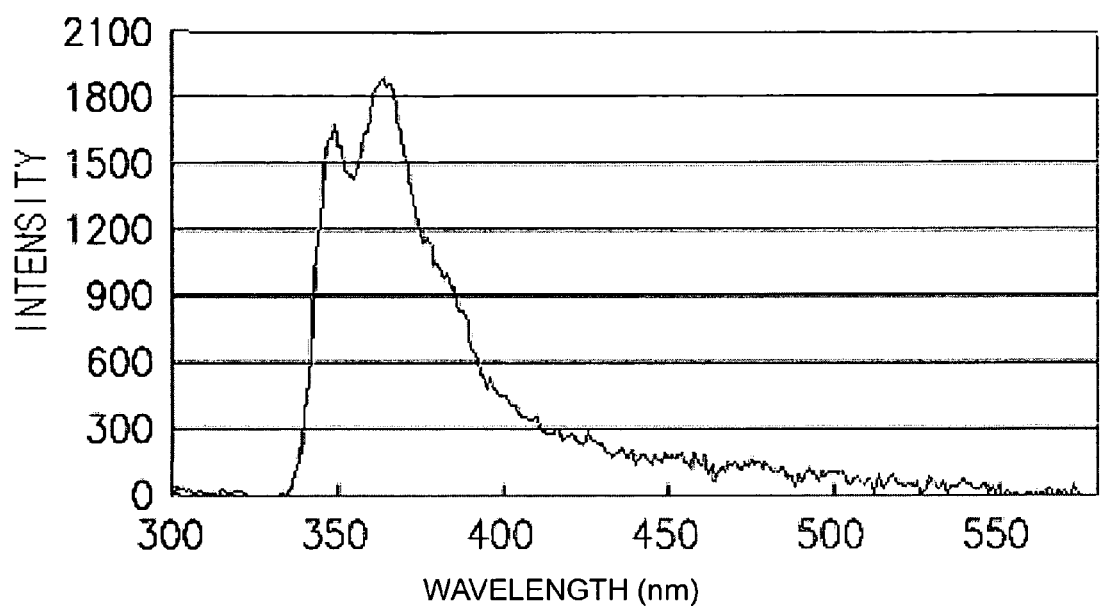
FIG. 3 is a PL spectrum of a film including a compound of Formula 4.

The compound of Formula 4 and polymethylmethacrylate (PMMA) were mixed at a ratio of 1:15 (w/w) and dissolved in chloroform. The resultant mixture was spin coated on a glass substrate (thickness: 1.0 mm, 50 mm×50 mm) to form a thin film and PL characteristics were evaluated. As a result, the maximal light intensity was observed at 365 nm (FIG. 3). Color purity corresponded to the CIE coordinate of x=0.1523, y=0.1235 in the NTSC chromaticity diagram.

Thermogravimetric analysis (TGA) and differential scanning calorimetry (DSC) analysis of the compound of Formula 4 were carried out. TGA was carried out under a $N_2$ gas atmosphere from room temperature to 600° C., with increasing temperature at a rate of 10° C./min. DSC analysis was carried out under $N_2$ gas atmosphere from room temperature to 400° C.

Figure 4:
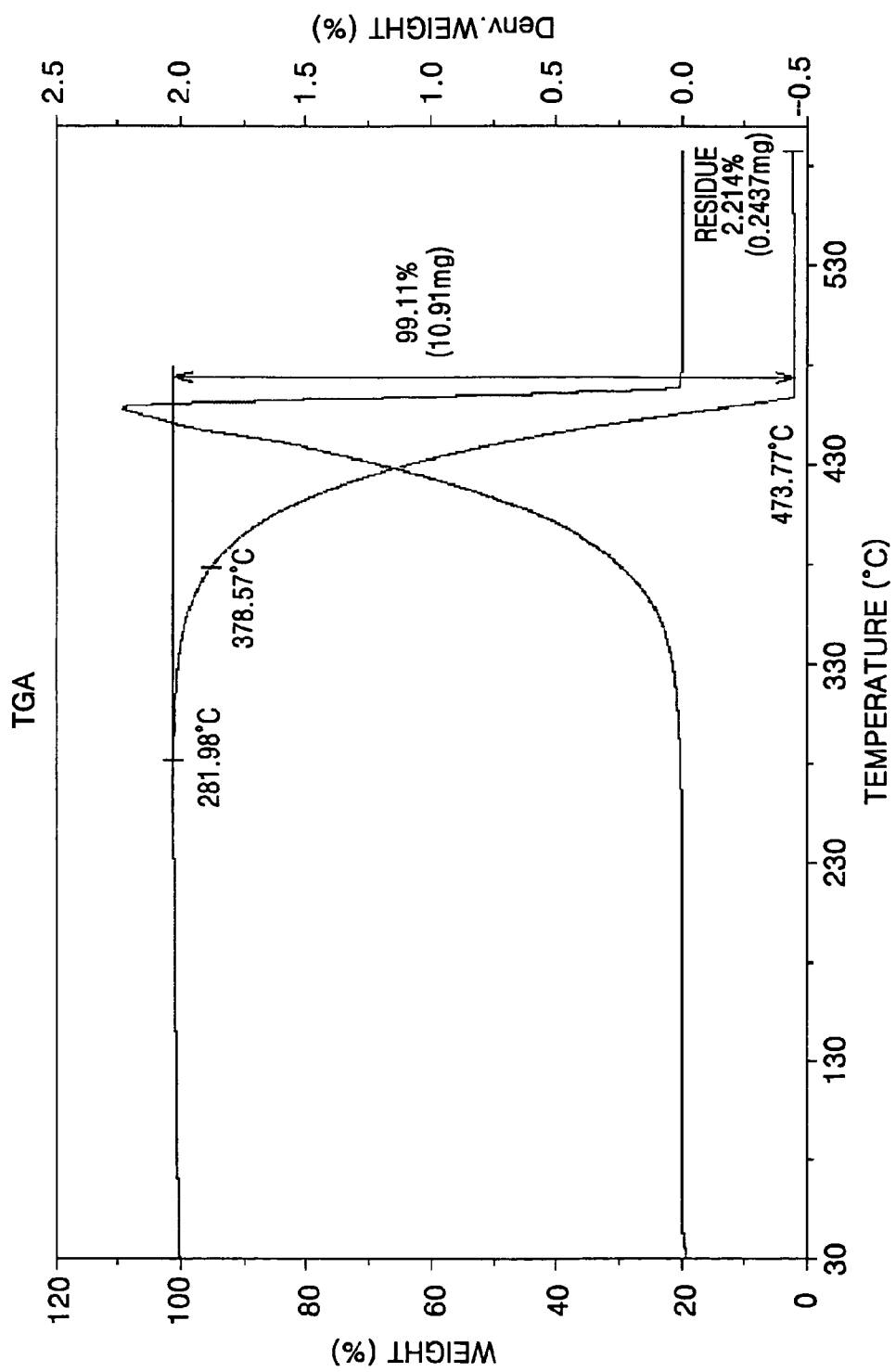
FIG. 4 is a graph illustrating the results of a thermogravimetric analysis (TGA) of the compound of Formula 4.
Figure 5:
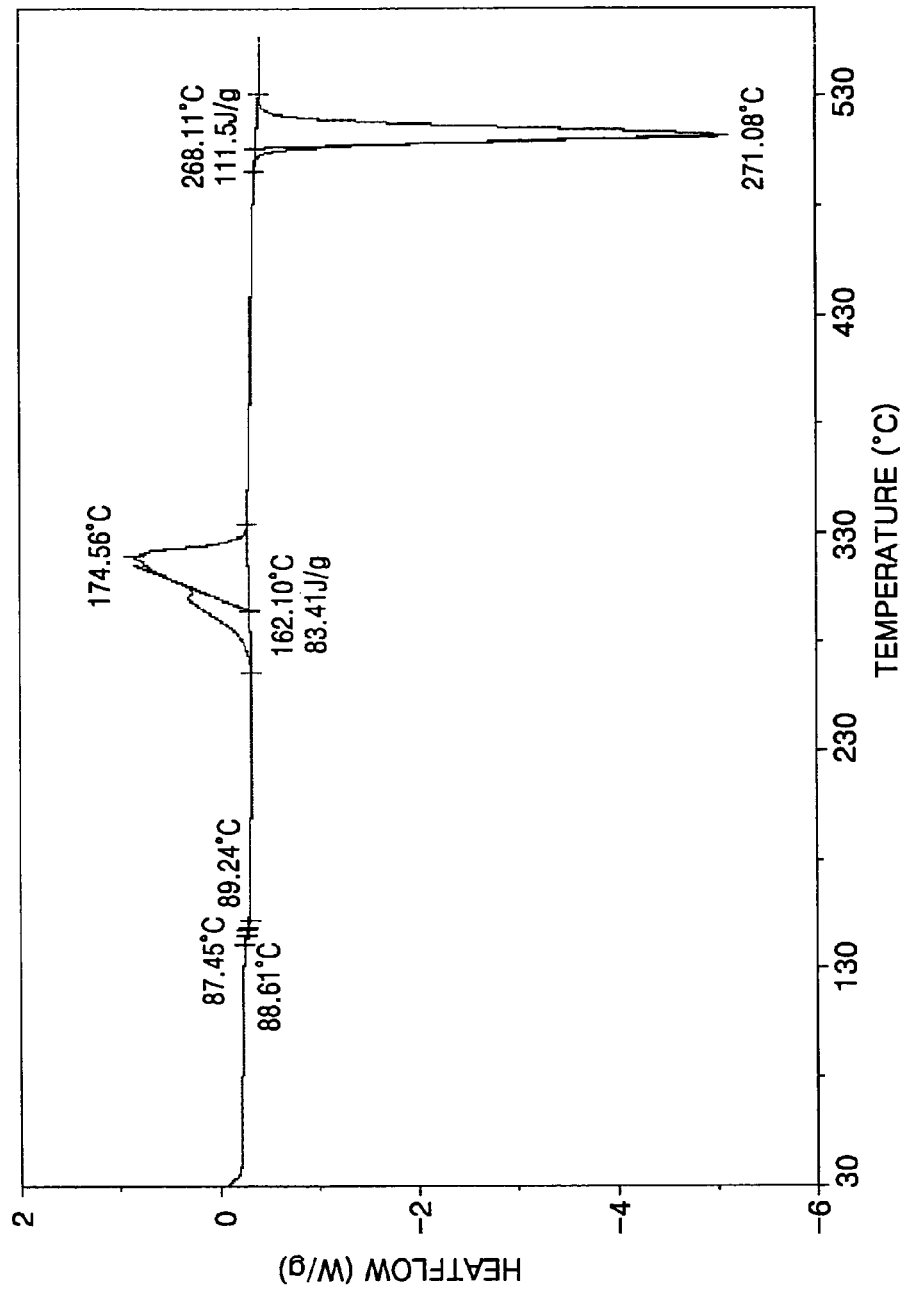
FIG. 5 is a graph illustrating the results of a differential scanning calorimetry (DSC) analysis of the compound of Formula 4.

As a result, the compound of Formula 4 exhibited Td of 379° C., Tg of 89° C., and Tm of 271° C. (FIGS. 4 and 5).

UV absorption spectrum and ionic potential were measured using a photoelectron spectrometer (Riken-Keiki AC-2). As a result, the HOMO (Highest Occupied Molecular Orbital) energy level and the LUMO (Lowest Occupied Molecular Orbital) energy level of the compound of Formula 4 were 5.92 and 2.43 eV, respectively, and the Eg was 3.49 eV.

Synthesis of Compound of Formula 5

The intermediate (A') (710 mg, 2.2 mmol) was dissolved in THF (10 mL) and n-butyllithium (0.92 mL, 2.3 mmol, 2.5 equiv.) in n-hexane at −78° C. was dropwise added thereto, followed by stirring for one hour. Dichlorodiphenylsilane (0.205 mL, 1.0 mmol) was added to the resultant mixture and stirred at −78° C. for one hour, and then at room temperature for 5 hours.

When the reaction was completed, an ammonium hydroxide solution (1 ml) was added to the reaction mixture, stirred for one hour, and extracted three times with ethylacetate (10 mL). A combined organic layer was dried over $MgSO_4$, and a solvent was removed. An obtained residue was purified by silica-gel column chromatography to give the compound of Formula 5 as a white solid (335 mg, yield 50%) with the following spectra: $^1$H-NMR ($CDCl_3$, 300 MHz) δ (ppm) 8.13 (d, 4H), 7.88 (d, 4H), 7.72 (dd, 4H), 7.65 (d, 4H), 7.53-7.46 (m, 10H), 7.40 (t, 4H), 7.28 (t, 4H) and $^{13}$C NMR ($CDCl_3$, 100 MHz) δ (ppm) 140.5, 139.2, 137.9, 136.4, 133.6, 133.1, 130.0, 128.2, 126.3, 125.9, 123.5, 120.3, 120.1, 109.9.

Figure 6:
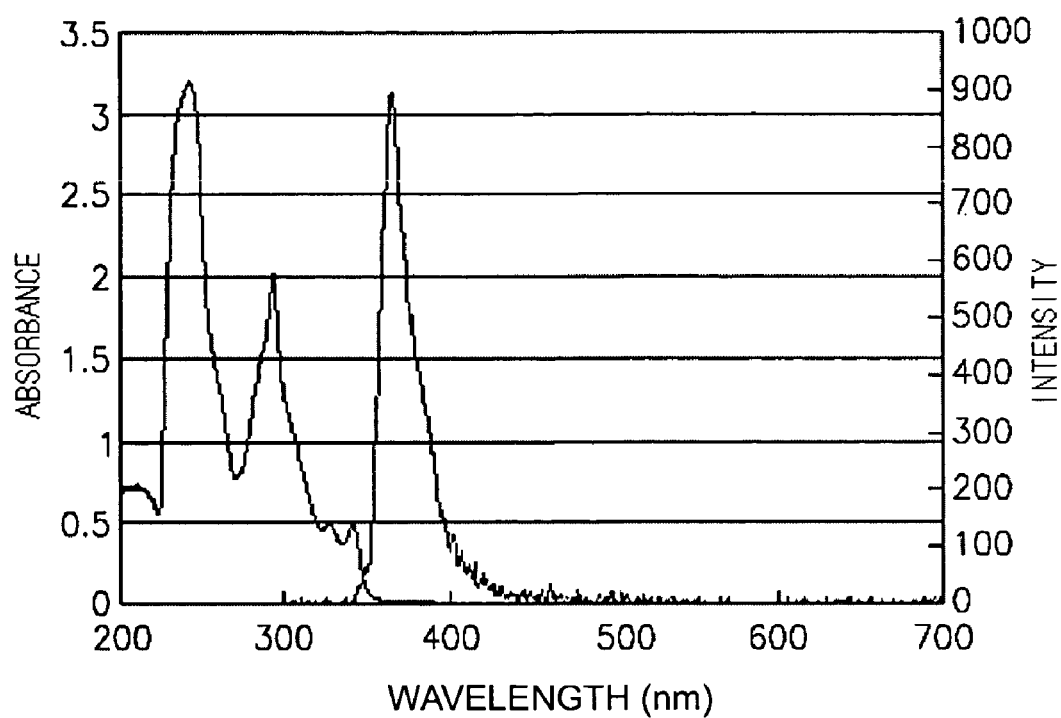
FIG. 6 is a PL spectrum of a solution containing a compound of Formula 5.

The compound of Formula 5 was diluted to 0.2 mM in $CHCl_3$ and a UV spectrum was measured. The UV spectrum of the diluted solution showed the maximal absorbance at 293 nm. Also, the compound of Formula 5 was diluted to 10 mM in $CHCl_3$, and a PL spectrum was measured at 293 nm. The PL spectrum of the diluted solution showed the maximal light intensity at 365 nm (FIG. 6). Color purity corresponded to the CIE coordinate of x=0.2166, y=0.1401 in the NTSC chromaticity diagram.

Figure 7:
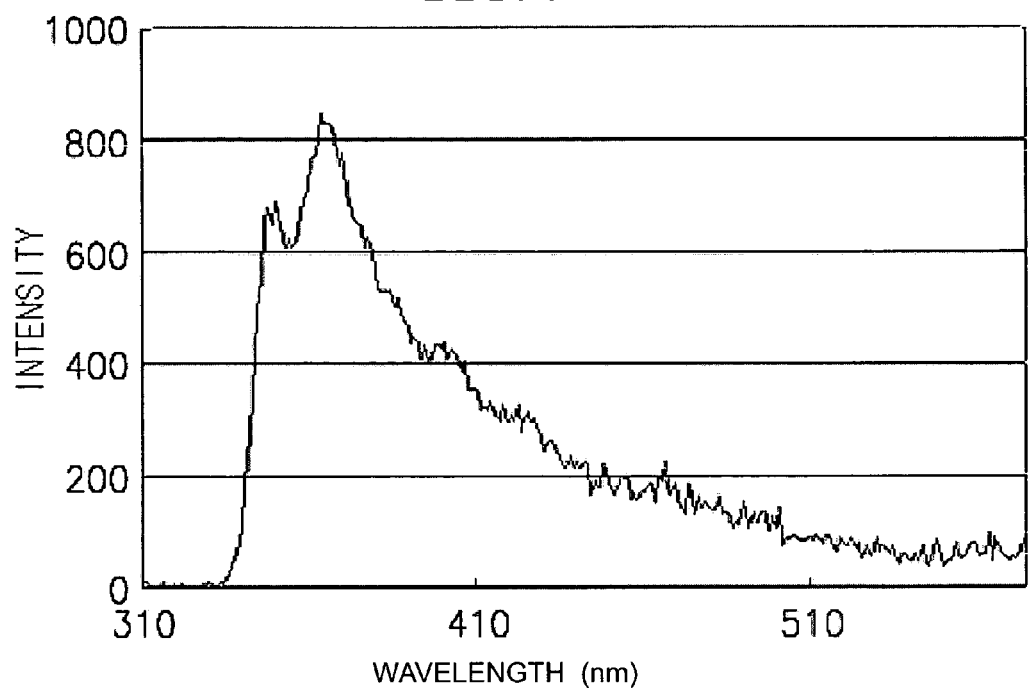
FIG. 7 is a PL spectrum of a film including the compound of Formula 5.

The compound of Formula 5 and PMMA were mixed at a ratio of 1:15 (w/w) and dissolved in chloroform. The resultant mixture was spin coated on a glass substrate (thickness: 1.0 mm, 50 mm×50 mm) to form a thin film, and the PL spectrum was measured. As a result, the maximal light intensity was observed at 364 nm (FIG. 7). Color purity corresponded to the CIE coordinate of x=0.1921, y=0.2018 in the NTSC chromaticity diagram.

UV absorption spectrum and ionic potential were measured using AC-2. As a result, the HOMO energy level and the LUMO energy level of the compound of Formula 5 were 6.09 and 2.61 eV, respectively, and the Eg was 3.49 eV.

TGA and DSC analysis of the compound of Formula 5 were carried out. TGA was carried out under a $N_2$ gas atmosphere from room temperature to 600° C., with increasing temperature at a rate of 10° C./min. DSC analysis was carried out under $N_2$ gas atmosphere from room temperature to 400° C.

As a result, the compound of Formula 5 exhibited Td of 393° C. and Tg of 109° C.

Synthesis 2. Preparation of Compound of Formula 6

The compound of Formula 6 was synthesized according to Scheme 4 below.

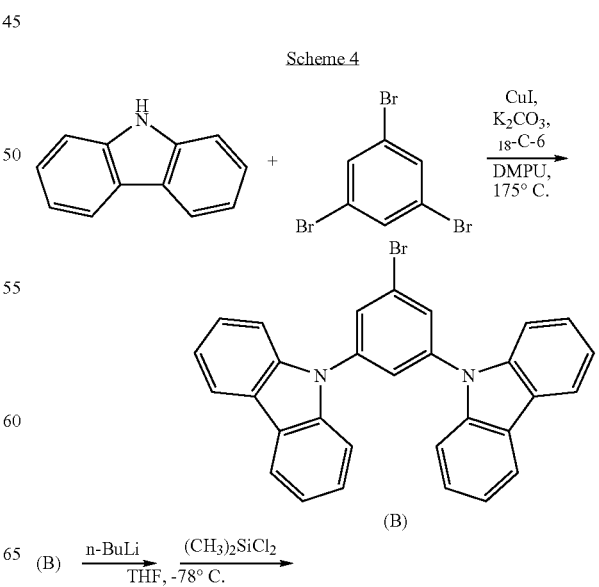

Scheme 4

-continued

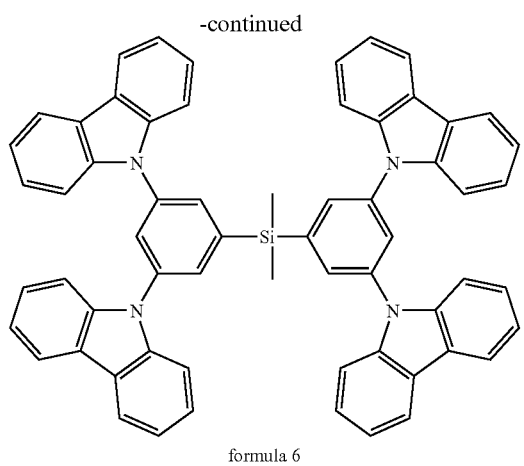

formula 6

Synthesis of Intermediate (B)

Carbazole (1 g, 6 mmol), 1,3,5-tribromobenzene (944 mg, 6 mmol), CuI (50 mg, 0.6 mmol), $K_2CO_3$ (3 g, 48 mmol), and 18-Crown-6 (30 mg, 0.24 mmol) were dissolved in DMPU (15mL) and heated at 175° C. for 8 hours.

The resultant mixture was cooled to room temperature, and the solids were filtered. A little ammonia water was then added to a filtrate, and the filtrate was washed three times with diethylether (20 mL). A washed diethylether layer was dried over $MgSO_4$ and then dried under reduced pressure to obtain a crude product. The crude product was purified by silica-gel column chromatography to give the intermediate (B) as a white solid (560 mg, yield 20%) having the following spectra: $^1$H-NMR ($CDCl_3$, 400 MHz) δ (ppm) 8.12 (d, 4H), 7.84 (d, 2H), 7.77 (t, 1H), 7.53 (d, 4H), 7.45 (dt, 4H), 7.31 (dt, 4H) and $^{13}$C NMR ($CDCl_3$, 100 MHz) δ (ppm) 140.4, 140.2, 134.4, 128.6, 126.3, 123.9, 123.8, 120.7, 120.5, 109.5.

Synthesis of Compound of Formula 6

The intermediate (B) (200 mg, 0.41 mmol) was dissolved in THF (3 mL), and n-butyllithium (0.2 mL, 0.49 mmol, 2.5 equiv.) in n-hexane at −78° C. was then dropwise added thereto, followed by stirring for one hour. Dichloromethylsilane (0.02 mL, 0.16 mmol) was added to the resultant mixture and stirred at −78° C. for one hour, and then at room temperature for 5 hours.

When the reaction was completed, an ammonium hydroxide solution (1 ml) was added to the reaction mixture, stirred for one hour, and extracted three times with ethylacetate (each 5 mL). A combined ethylacetate layer was dried over $MgSO_4$, and a solvent was removed. An obtained residue was purified by silica-gel column chromatography to give the compound of Formula 6 as a white solid (70 mg, yield 49%) having the following spectra: $^1$H NMR ($CDCl_3$, 300 MHz) δ (ppm) 8.16-8.11 (m, 8H), 7.91 (d, 4H), 7.84 (t, 2H), 7.44 (d, 8H), 7.32-7.24 (m, 16H), 0.78 (s, 6H) and $^{13}$C NMR ($CDCl_3$, 100 MHz) δ (ppm) 141.7, 140.5, 139.3, 131.0, 126.4, 126.2, 123.6, 120.5, 120.4, 109.5, −2.5.

Figure 8:
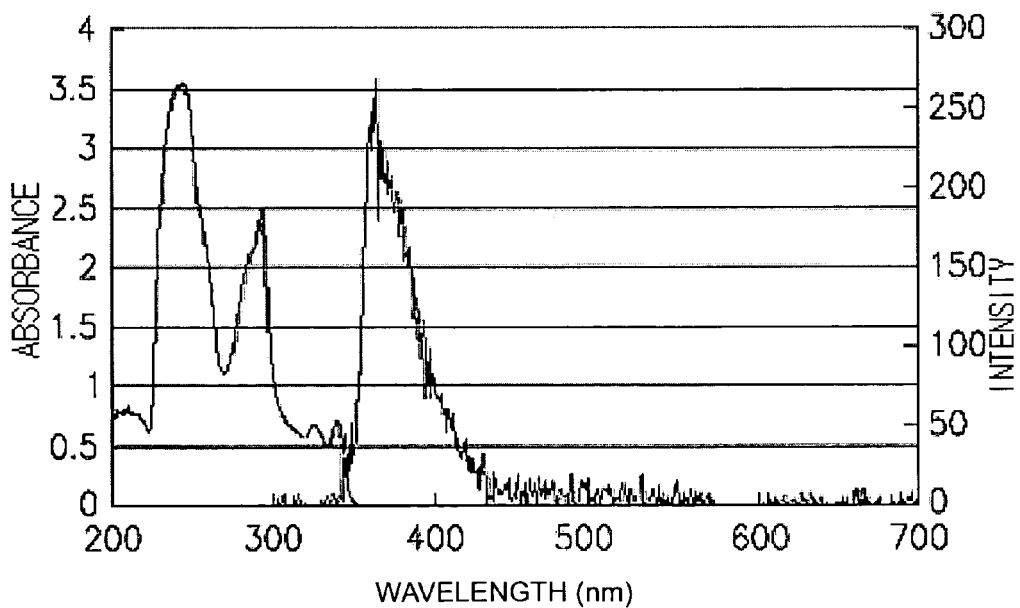
FIG. 8 is a PL spectrum of a solution containing a compound of Formula 6.

The compound of Formula 6 was diluted to 0.2 mM in $CHCl_3$ and a UV spectrum was measured. The UV spectrum of the diluted solution showed the maximal absorbance at 292.5 nm. Also, the compound of Formula 6 was diluted to 10 mM in $CHCl_3$ and a PL spectrum was measured at 292.5 nm. The PL spectrum of the diluted solution showed a peak light intensity at 364 nm (FIG. 8). Color purity corresponded to the CIE coordinate of x=0.2241, y=0.1926 in the NTSC chromaticity diagram.

Figure 9:
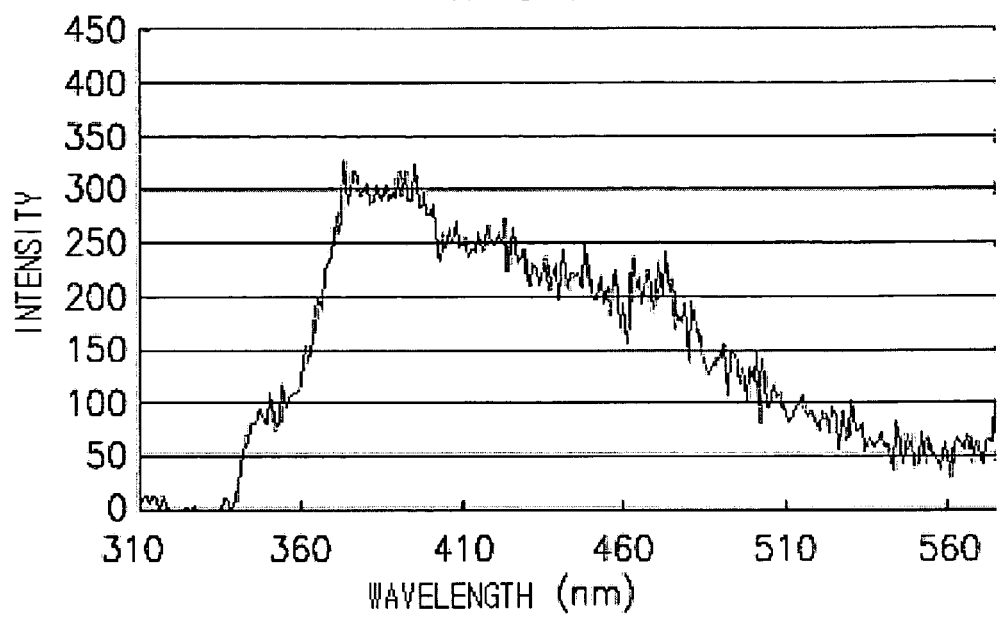
FIG. 9 is a PL spectrum of a film including the compound of Formula 6.

The compound of Formula 6 and PMMA were mixed at a ratio of 1:15 (w/w) and dissolved in chloroform. The resultant mixture was spin coated on a glass substrate (thickness: 1.0 mm, 50 mm×50 mm) to form a thin film and PL spectrum was measured. As a result, a peak light intensity was observed at 373 nm (FIG. 9). Color purity corresponded to the CIE coordinate of x=0.1878, y=0.2088 in the NTSC chromaticity diagram, and Eg was 3.51 eV.

TGA and DSC analysis of the compound of Formula 6 were carried out. TGA was carried out under $N_2$ gas atmosphere from room temperature to 600° C., with increasing temperature at a rate of 10° C./min. DSC analysis was carried out under $N_2$ gas atmosphere from room temperature to 400° C.

As a result, the compound of Formula 6 exhibited Td of 409° C. and Tg of 130° C.

EXAMPLE 1

An ITO substrate (10 $\Omega/cm^2$) (CORNING CO.) was used as an anode. IDE406 (IDEMITSU CO.) was vacuum deposited on the substrate to form a hole injection layer with a thickness of 600 Å. Then, IDE320 (IDEMITSU CO.) was vacuum deposited to a thickness of 300 Å on the hole injection layer to form a hole transport layer. A mixture (90:10, w/w) of the compound of Formula 4 and TEB002 (COVION CO.) was vacuum deposited on the hole transport layer to form a light-emitting layer with a thickness of 300 Å.

Then, BAlq was vacuum deposited on the light-emitting layer to form a hole blocking layer with a thickness of 50 Å. $Alq_3$ was then vacuum deposited on the hole blocking layer to form an electron transport layer with a thickness of 200 Å. LiF and Al were sequentially vacuum deposited to a thickness of 10 Å and 3,000 Å, respectively, on the electron transport layer to form a cathode. Accordingly, an organic electroluminescent device was completed.

EXAMPLE 2

An organic electroluminescent device was manufactured in the same manner as in Example 1 except that a mixture (80:20, w/w) of the compound of Formula 4 and TEB002 (COVION CO.) was used in the formation of the light-emitting layer, instead of the mixture (90:10, w/w) of the compound of Formula 4 and TEB002 (COVION CO.).

EXAMPLE 3

An organic electroluminescent device was manufactured in the same manner as in Example 1 except that a mixture (90:10, w/w) of the compound of Formula 5 and TEB002 (COVION CO.) was used in the formation of the light-emitting layer, instead of the mixture (90:10, w/w) of the compound of Formula 4 and TEB002 (COVION CO.).

EXAMPLE 4

An organic electroluminescent device was manufactured in the same manner as in Example 1 except that a mixture (90:10, w/w) of the compound of Formula 6 and TEB002 (COVION CO.) was used in the formation of the light-emitting layer, instead of the mixture (90:10, w/w) of the compound of Formula 4 and TEB002 (COVION CO.).

The driving voltage, current density, luminance, current efficiency, power efficiency, and color coordinate characteristics of the organic electroluminescent devices of Examples 1-2 were measured, and the results are presented in Table 1 below.

TABLE 1

| Section | Voltage | Current | Luminance | Current | Power | Color coordinate |
|---|---|---|---|---|---|---|
| Example 1 | 6.5 | 2.4 | 100 | 4.25 | 2.05 | (0.14, 0.19) |
| Example 2 | 6.7 | 5.5 | 100 | 1.7 | 0.80 | (0.15, 0.20) |

As seen from Table 1, the organic electroluminescent devices of Examples 1 and 2 exhibited excellent voltage, current density, luminance, current and power efficiency, and color coordinate characteristics.

Figure 10:
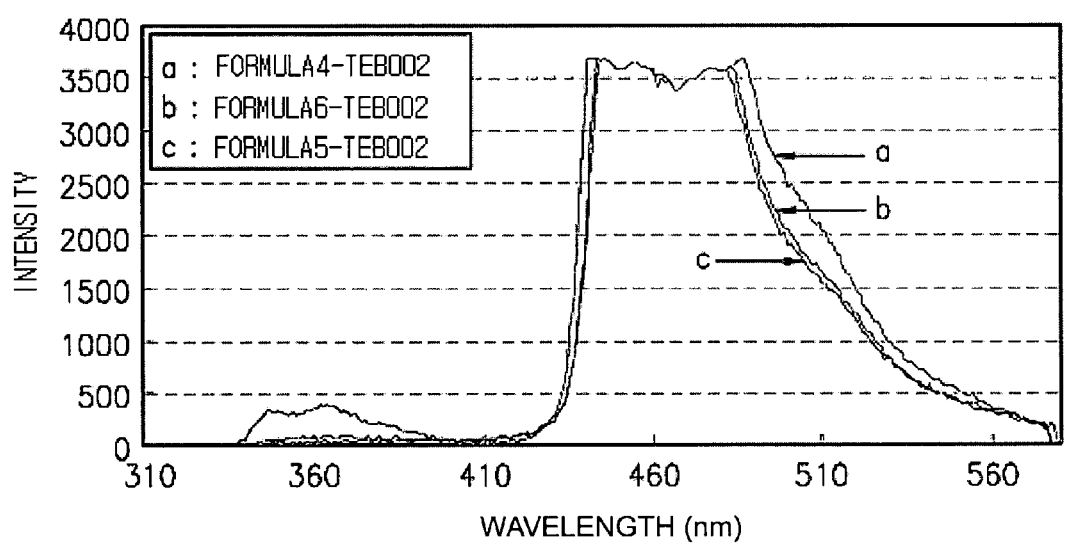
FIG. 10 is a PL spectrum of films including a mixture of the compound of Formula 4 and TEB002 (COVION CO.), a mixture of the compound of Formula 5 and TEB002 (COVION CO.), and a mixture of the compound of Formula 6 and TEB002 (COVION CO.).

Each of the mixtures for the light-emitting layers of Examples 1, 3, and 4 was mixed with PMMA at a ratio of 1:15 (w/w), and was then dissolved in chloroform. The resultant mixture was spin coated to form a thin film, and PL characteristics were evaluated. The results are presented in Table 2 below and FIG. 10.

TABLE 2

| Section | Composition of Light-Emitting Layer | PL | Color coordinate (x, y) |
|---|---|---|---|
| Example 1 | Mixture of Compound of Formula 4 and TEB002 (90:10, w/w) | 443 | (0.1397, 0.2063) |
| Example 3 | Mixture of Compound of Formula 5 and TEB002 (90:10, w/w) | 446 | (0.1402, 0.1928) |
| Example 4 | Mixture of Compound of Formula 6 and TEB002 (90:10, w/w) | 444 | (0.1416, 0.1915) |

As seen from Table 2, the energy transition of the compound of Formula 4 to a blue phosphorescent dopant, TEB002 occurred efficiently.

A CBP based silicon compound of the present invention has excellent blue light emission characteristics and hole transfer capability. The CBP based silicon compound may be used as a blue light emission material or as a host material for various phosphorescent or fluorescent dopants emitting red, green, blue, or white light. Therefore, an organic electroluminescent device using the CBP based silicon compound has excellent characteristics such as a high efficiency, a high luminance, a long life span, and a low power consumption.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. A compound represented by Formula 1:

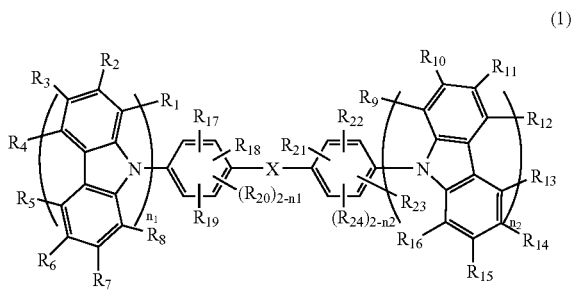

(1)

wherein,

X is —Si(A$_1$)(A$_2$)- or Se, n$_1$ and n$_2$ are independently 1 or 2 when X is Se, and n$_1$ and n$_2$ are 2 when X is —Si(A$_1$)(A$_2$)-, and A$_1$, A$_2$, and R$_1$ to R$_{24}$ are independently a hydrogen atom, a substituted or unsubstituted alkyl group of C$_1$-C$_{30}$, a substituted or unsubstituted acyl group of C$_1$-C$_{30}$, a substituted or unsubstituted alkoxycarbonyl group of C$_1$-C$_{30}$, a substituted or unsubstituted alkoxy group of C$_1$-C$_{30}$, a substituted or unsubstituted alkenyl group of C$_2$-C$_{30}$, a substituted or unsubstituted alkynyl group of C$_2$-C$_{30}$, a substituted or unsubstituted alkylcarboxyl group of C$_2$-C$_{30}$, a substituted or unsubstituted aryl group of C$_6$-C$_{30}$, a substituted or unsubstituted aralkyl group of C$_6$-C$_{30}$, a substituted or unsubstituted aralkyloxy group of C$_6$-C$_{30}$, a substituted or unsubstituted heteroaryl group of C$_2$-C$_{30}$, a substituted or unsubstituted heteroaryloxy group of C$_2$-C$_{30}$, a substituted or unsubstituted aryloxy group of C$_6$-C$_{30}$, a substituted or unsubstituted cycloalkyl group of C$_4$-C$_{30}$, —N(R)(R') (provided that R and R' are independently a hydrogen, an alkyl group of C$_1$-C$_{30}$, an aryl group of C$_6$-C$_{30}$, or a heteroaryl group of C$_2$-C$_{30}$), cyano, hydroxy, or carboxyl, or at least an adjacent two of R$_1$ to R$_{24}$ are connectable to form a ring.

2. The compound of claim 1, wherein n$_1$ and n$_2$ are 2.

3. The compound of claim 2, wherein the compound is further represented by Formula 3:

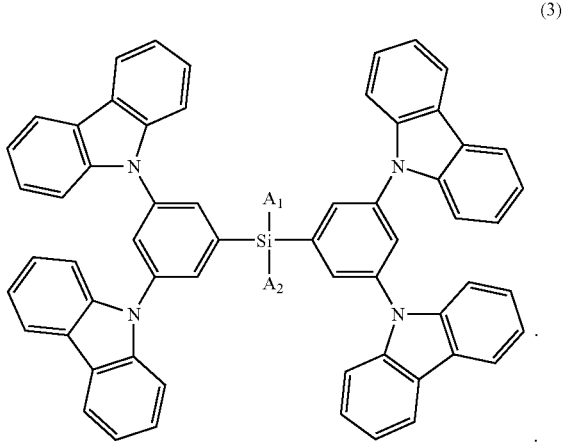

(3)

4. The compound of claim 1, which is selected from the group consisting of compounds represented by Formulas 6, 7, 10, 11, 15, 16 or 17:

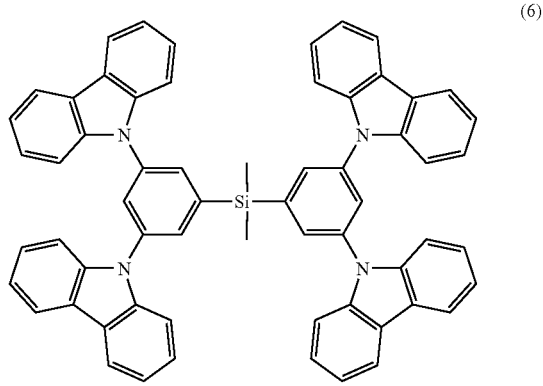

(6)

-continued

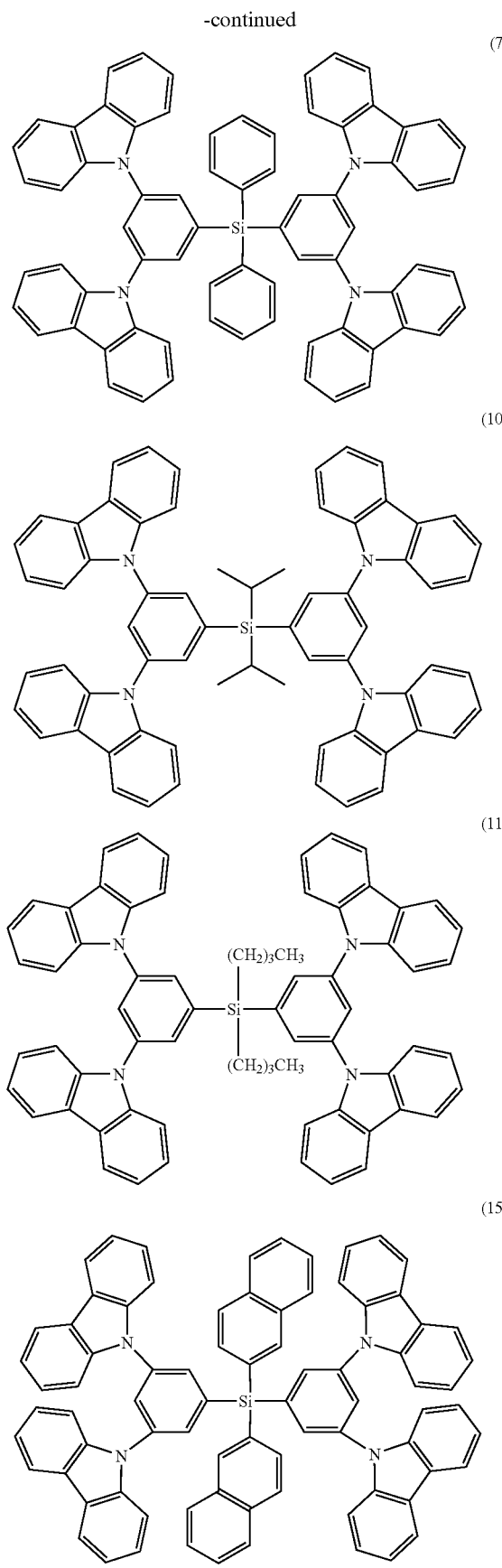

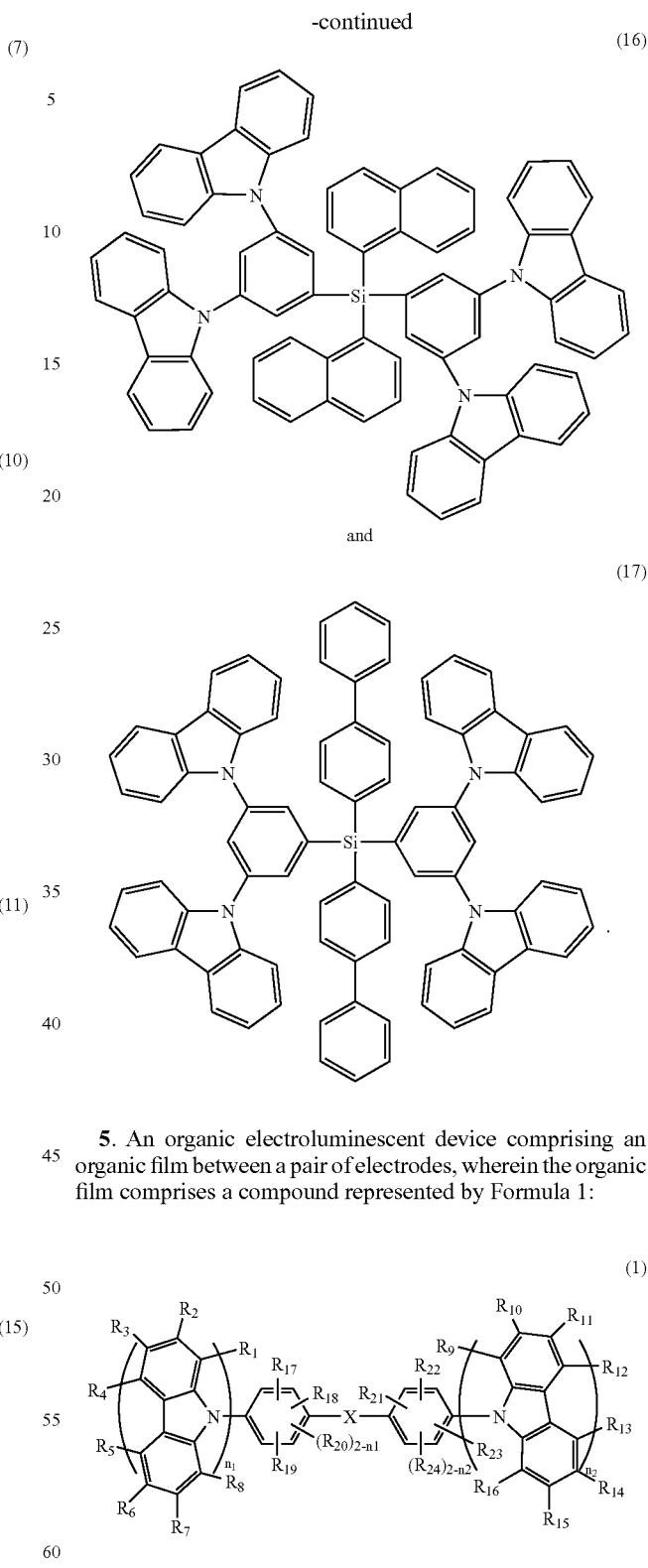

5. An organic electroluminescent device comprising an organic film between a pair of electrodes, wherein the organic film comprises a compound represented by Formula 1:

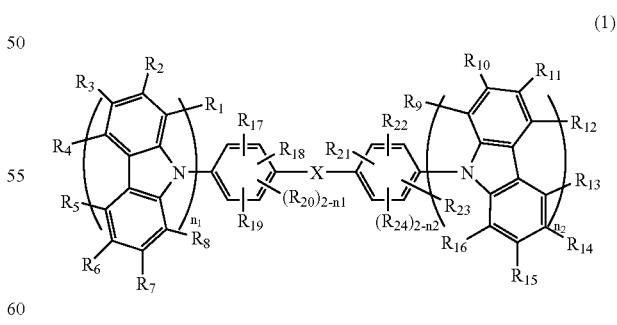

wherein,

X is —Si($A_1$)($A_2$)- or Se, $n_1$ and $n_2$ are independently 1 or 2 when X is Se and $n_1$ and $n_2$ are 2 when X is —Si($A_1$)($A_2$)-, and $A_1$, $A_2$, and $R_1$ to $R_{24}$ are independently a hydrogen atom, a substituted or unsubstituted alkyl group of $C_1$-$C_{30}$, a substituted or unsubstituted acyl group of $C_1$-$C_{30}$, a substituted or unsubstituted alkoxycarbonyl group of $C_1$-$C_{30}$, a substituted or unsubstituted alkoxy group of $C_1$-$C_{30}$, a substituted or unsubstituted alkenyl group of $C_2$-$C_{30}$, a substituted or unsubstituted alkynyl group of $C_2$-$C_{30}$, a substituted or unsubstituted alkylcarboxyl group of $C_2$-$C_{30}$, a substituted or unsubstituted aryl group of $C_6$-$C_{30}$, a substituted or unsubstituted aralkyl group of $C_6$-$C_{30}$, a substituted or unsubstituted aralkyloxy group of $C_6$-$C_{30}$, a substituted or unsubstituted heteroaryl group of $C_2$-$C_{30}$, a substituted or unsubstituted heteroaryloxy group of $C_2$-$C_{30}$, a substituted or unsubstituted aryloxy group of $C_6$-$C_{30}$, a substituted or unsubstituted cycloalkyl group of $C_4$-$C_{30}$, —N(R)(R') (provided that R and R' are independently a hydrogen, an alkyl group of $C_1$-$C_{30}$, an aryl group of $C_6$-$C_{30}$, or a heteroaryl group of $C_2$-$C_{30}$), cyano, hydroxy, or carboxyl, or at least an adjacent two of $R_1$ to $R_{24}$ are connectable to form a ring.

6. The organic electroluminescent device of claim 5, wherein the organic film is a light-emitting layer.

7. The organic electroluminescent device of claim 6, wherein the light-emitting layer comprises a visible light phosphorescent or fluorescent dopant.

8. The organic electroluminescent device of claim 5, wherein the organic film is a hole injection layer or a hole transport layer.

9. The organic electroluminescent device of claim 5, wherein $n_1$ and $n_2$ of the compound are 2.

10. The organic electroluminescent device of claim 9, wherein the compound is further represented by Formula 3:

(3)

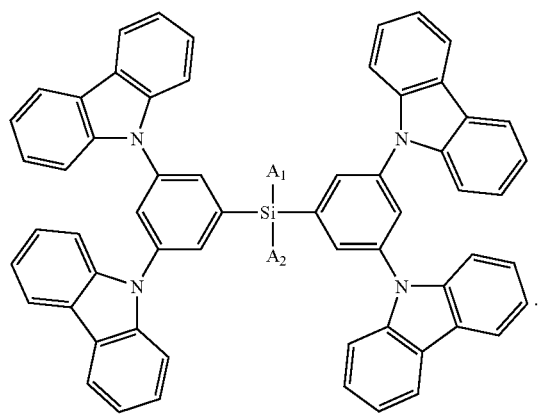

11. The organic electroluminescent device of claim 5, wherein the compound is selected from the group consisting of compounds represented by Formulas 6, 7, 10, 11, 15, 16 or 17:

(6)

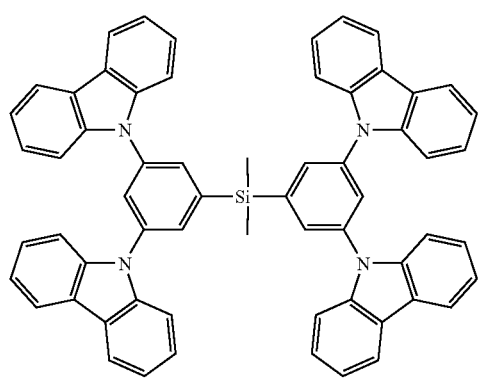

-continued (7)

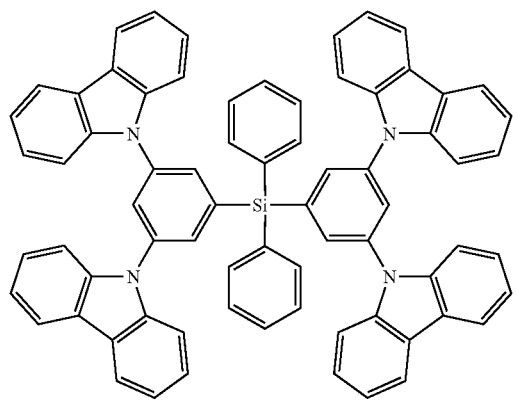

(10)

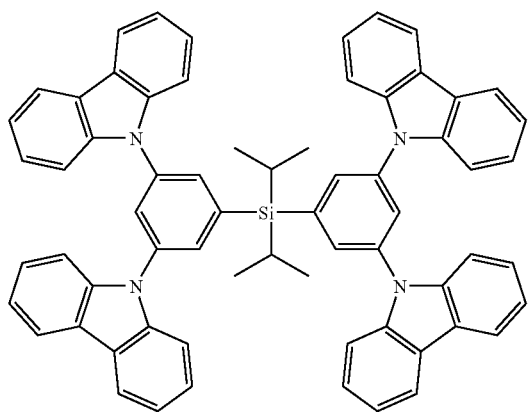

(11)

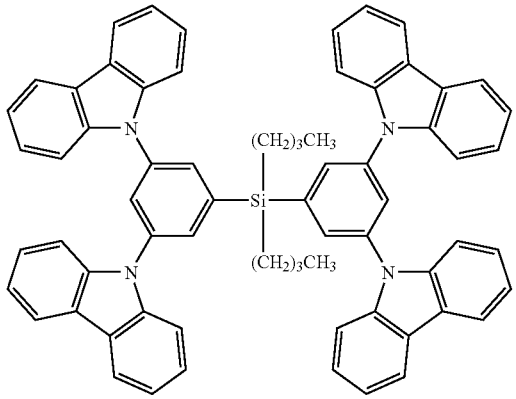

(15)

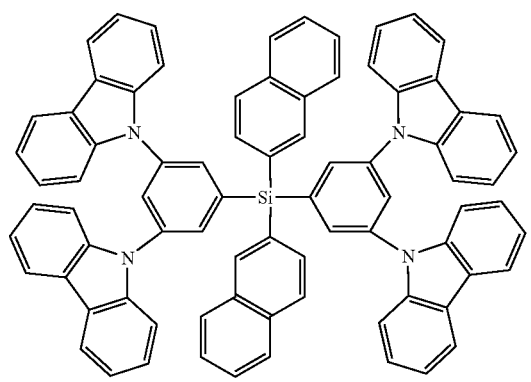

-continued (16)

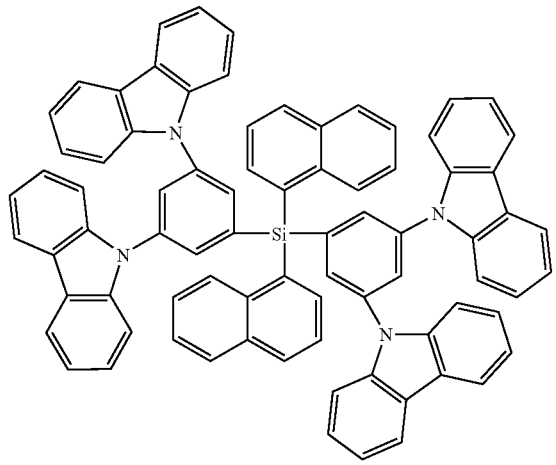

and (17)

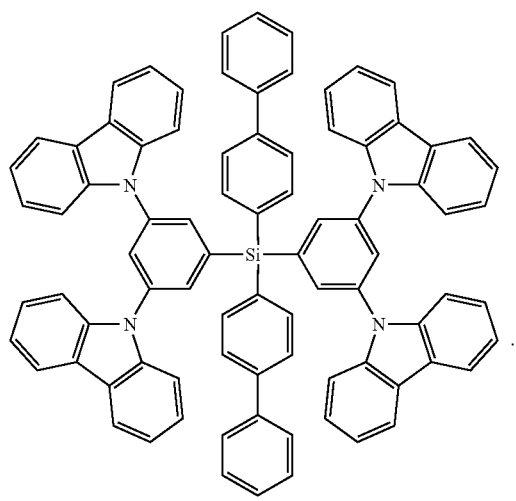

12. An organic electroluminescent device comprising a plurality of layers to facilitate emission of light between a pair of electrodes, wherein a light emitting layer of the plurality of layers comprises a compound represented by Formula 1:

(1)

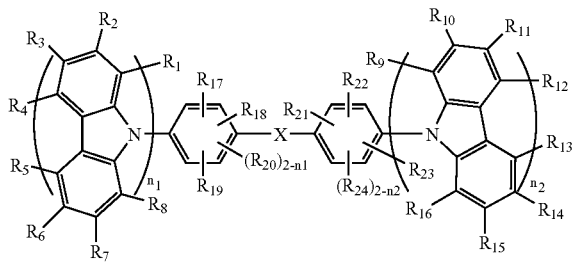

wherein,
X is —Si($A_1$)($A_2$)- or Se,
$n_1$ and $n_2$ are independently 1 or 2 when X is Se and $n_1$ and $n_2$ are 2 when X is —Si($A_1$)($A_2$)-, and
$A_1$, $A_2$, and $R_1$ to $R_{24}$ are independently a hydrogen atom, a substituted or unsubstituted alkyl group of $C_1$-$C_{30}$, a substituted or unsubstituted acyl group of $C_1$-$C_{30}$, a substituted or unsubstituted alkoxycarbonyl group of $C_1$-$C_{30}$, a substituted or unsubstituted alkoxy group of $C_1$-$C_{30}$, a substituted or unsubstituted alkenyl group of $C_2$-$C_{30}$, a substituted or unsubstituted alkynyl group of $C_2$-$C_{30}$, a substituted or unsubstituted alkylcarboxyl group of $C_2$-$C_{30}$, a substituted or unsubstituted aryl group of $C_6$-$C_{30}$, a substituted or unsubstituted aralkyl group of $C_6$-$C_{30}$, a substituted or unsubstituted aralkyloxy group of $C_1$-$C_{30}$, a substituted or unsubstituted heteroaryl group of $C_2$-$C_{30}$, a substituted or unsubstituted heteroaryloxy group of $C_2$-$C_{30}$, a substituted or unsubstituted aryloxy group of $C_6$-$C_{30}$, a substituted or unsubstituted cycloalkyl group of $C_4$-$C_{30}$, —N(R)(R') (provided that R and R' are independently a hydrogen, an alkyl group of $C_1$-$C_{30}$, an aryl group of $C_6$-$C_{30}$, or a heteroaryl group of $C_2$-$C_{30}$), cyano, hydroxy, or carboxyl, or at least an adjacent two of $R_1$ to $R_{24}$ are connectable to form a ring.

13. The organic electroluminescent device of claim 12, wherein the light-emitting layer comprises a visible light phosphorescent or fluorescent dopant.

14. The organic electroluminescent device of claim 12, wherein the plurality of layers comprises: a hole injection layer, a hole transport layer, the light-emitting layer, a hole blocking layer, a electron transport layer, and a electron injection layer.

15. The organic electroluminescent device of claim 12, wherein $n_1$ and $n_2$ are 2.

16. The organic electroluminescent device of claim 12, wherein the compound is further represented by Formula 3:

(3)

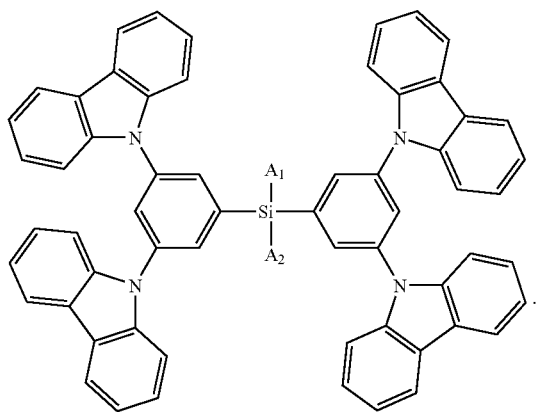

17. The organic electroluminescent device of claim 12, wherein the compound is selected from the group consisting of compounds represented by Formulas 6, 7, 10, 11, 15, 16 or 17:

(6)

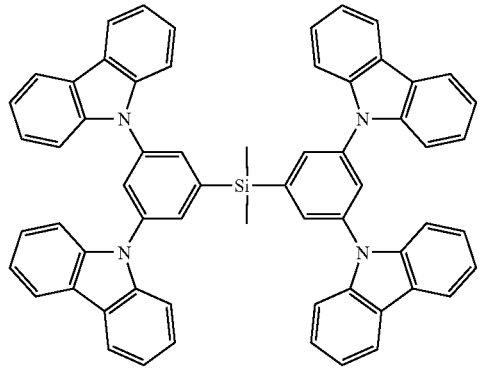

-continued
(7)
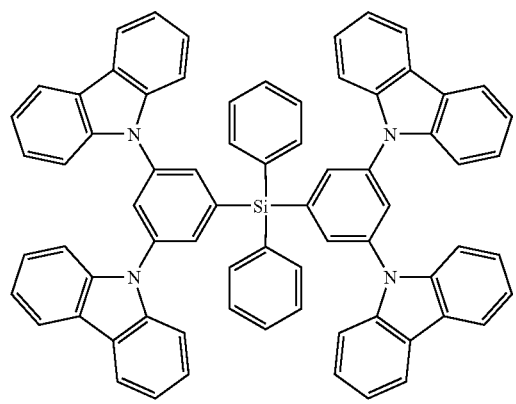
(10)
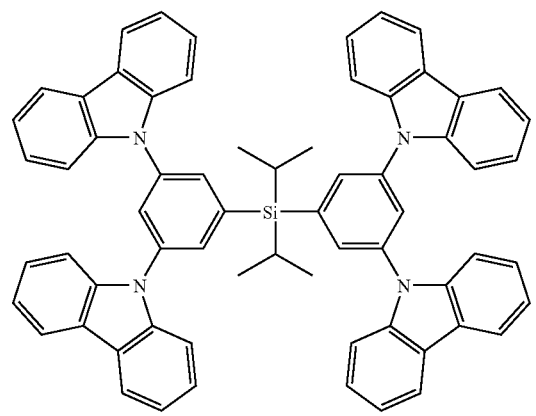
(11)
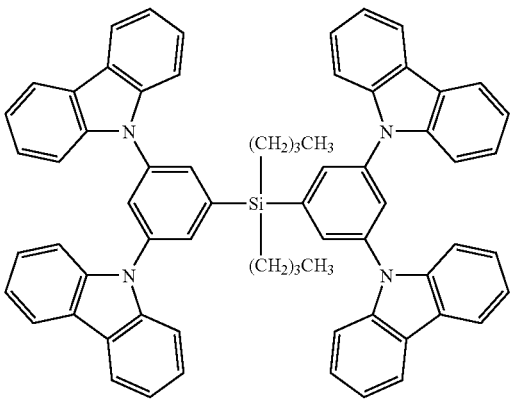
-continued
(15)
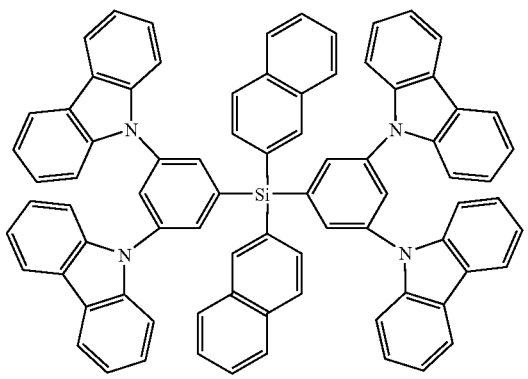
(16)
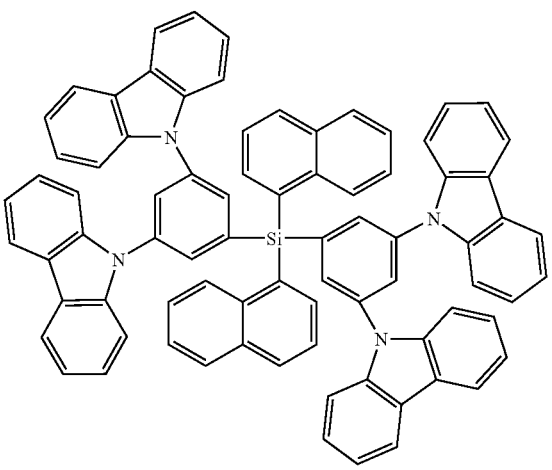
and
(17)
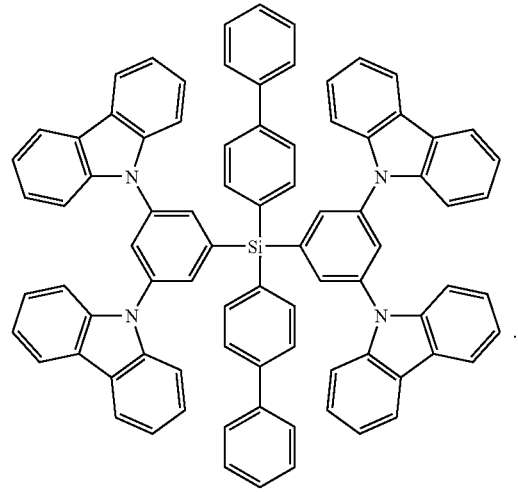
* * * * *

UNITED STATES PATENT AND TRADEMARK OFFICE
CERTIFICATE OF CORRECTION

PATENT NO.         : 7,413,817 B2
APPLICATION NO.    : 10/876843
DATED              : August 19, 2008
INVENTOR(S)        : Seok Jong Lee et al.

It is certified that error appears in the above-identified patent and that said Letters Patent is hereby corrected as shown below:

Column 26, line 7, change "$C_1$-$C_{30}$" to --$C_6$-$C_{30}$--.

Signed and Sealed this

Twenty-first Day of October, 2008

JON W. DUDAS
*Director of the United States Patent and Trademark Office*